(12) United States Patent
Nagao et al.

(10) Patent No.: US 9,627,625 B2
(45) Date of Patent: Apr. 18, 2017

(54) LIGHT-EMITTING DEVICE MATERIAL AND LIGHT-EMITTING DEVICE

(71) Applicant: TORAY INDUSTRIES, INC., Tokyo (JP)

(72) Inventors: Kazumasa Nagao, Tokyo (JP); Shinichi Matsuki, Otsu (JP); HIrotoshi Sakaino, Otsu (JP); Takeshi Arai, Otsu (JP); Tsuyoshi Tominaga, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 273 days.

(21) Appl. No.: 14/377,431

(22) PCT Filed: Feb. 13, 2013

(86) PCT No.: PCT/JP2013/053347
§ 371 (c)(1),
(2) Date: Aug. 7, 2014

(87) PCT Pub. No.: WO2013/122082
PCT Pub. Date: Aug. 22, 2013

(65) Prior Publication Data
US 2015/0084020 A1    Mar. 26, 2015

(30) Foreign Application Priority Data
Feb. 15, 2012 (JP) ................ 2012-030176

(51) Int. Cl.
| | |
|---|---|
| H01L 51/50 | (2006.01) |
| H01L 51/00 | (2006.01) |
| C09K 11/06 | (2006.01) |
| H05B 33/10 | (2006.01) |
| C07D 209/86 | (2006.01) |

(52) U.S. Cl.
CPC ........ *H01L 51/0061* (2013.01); *C07D 209/86* (2013.01); *C09K 11/06* (2013.01); *H01L 51/0072* (2013.01); *H01L 51/5016* (2013.01); *H01L 51/5056* (2013.01); *H01L 51/5072* (2013.01); *H01L 51/5088* (2013.01); *H05B 33/10* (2013.01); *C09K 2211/1007* (2013.01); *C09K 2211/1011* (2013.01); *C09K 2211/1029* (2013.01)

(58) Field of Classification Search
None
See application file for complete search history.

(56) References Cited

FOREIGN PATENT DOCUMENTS

| | | | |
|---|---|---|---|
| JP | H08-3547 A | 1/1996 | |
| JP | 9-249876 A | 9/1997 | |
| JP | 2008-135498 A | 6/2008 | |
| KR | 10-2009-0112137 A | 10/2009 | |
| KR | 10-2010-0079458 | * 7/2010 | ........... C07D 209/82 |
| KR | 2010-0079458 A | 7/2010 | |
| WO | WO2006/061759 A2 | 6/2006 | |
| WO | WO2010/095621 A1 | 8/2010 | |
| WO | WO2011/024451 A1 | 3/2011 | |
| WO | WO2011/055934 A2 | 5/2011 | |
| WO | WO2011/139055 A2 | 11/2011 | |
| WO | WO2011/162162 A1 | 12/2011 | |
| WO | WO2012/001986 A1 | 1/2012 | |

OTHER PUBLICATIONS

International Search Report for PCT International Application No. PCT/JP2013/053347 dated May 14, 2013.

* cited by examiner

*Primary Examiner* — Gregory Clark
(74) *Attorney, Agent, or Firm* — RatnerPrestia

(57) ABSTRACT

An organic thin film light-emitting element having both high luminous efficiency and high durability can be provided using a light-emitting element material that comprises a compound having a specified carbazole skeleton.

14 Claims, No Drawings

LIGHT-EMITTING DEVICE MATERIAL AND LIGHT-EMITTING DEVICE

CROSS REFERENCE TO RELATED APPLICATIONS

This is the U.S. National Phase application of PCT/JP2013/053347, filed Feb. 13, 2013, which claims priority to Japanese Patent Application No. 2012-030176, filed Feb. 15, 2012, the disclosures of each of these applications being incorporated herein by reference in their entireties for all purposes.

FIELD OF THE INVENTION

The present invention relates to a light-emitting device capable of converting electric energy into light, and a light-emitting device material to be used for the same. In particular, the present invention relates to a light-emitting device capable of being used for areas such as display devices, flat-panel displays, backlight, lighting, interior design, labels, signboards, electrophotography machines, and light signal generators, and also to a light-emitting device material to be used for the same.

BACKGROUND OF THE INVENTION

Researches on an organic thin-film light-emitting device in which electrons injected from a cathode and holes injected from an anode emit light when they are recombined in an organic fluorescent body held by both electrodes have been actively conducted in recent years. This light-emitting device is characteristic for high luminance light emission in the form of a thin type and under a low driving voltage, and multicolor light emission due to selection of a fluorescent material, and has been paid attention.

Such researches have undergone many studies for practical use since C. W. Tang et al. of Kodak Co., Ltd. showed that an organic thin-film device emits light at high luminance, and organic thin-film light-emitting devices have steadily come into practical use as they have been employed in main displays of mobile phones, and the like. However, there are still many technical problems and, especially, attainment of both increased efficiency and prolonged life of an device is one of the major problems.

The driving voltage of an device greatly depends on a carrier transporting material that transports carriers such as a hole and an electron to an emissive layer. Materials having a carbazole skeleton are known as materials to transport holes (hole transporting materials) (see, for example, Patent Literatures 1 to 3). The material having a carbazole skeleton is known to have high triplet energy (see, for example, Patent Literature 4), and is proposed to be used particularly as a material that confines triplet excitons from a phosphorescence emitting layer (see, for example, Patent Literature 5).

PATENT LITERATURE

[PTL 1] JP 8-3547 A
[PTL 2] KR 2010-0079458 A
[PTL 3] WO 2010/95621 A
[PTL 4] WO 2006/61759 A
[PTL 5] WO 2012/001986 A

SUMMARY OF THE INVENTION

Conventional technologies were difficult to reduce the driving voltage of an device sufficiently, and even if they had been able to reduce the driving voltage, the luminous efficiency and the durable life of an device were insufficient. Thus, technologies capable of realizing both high luminous efficiency and durable life have not been found yet.

An object of the present invention is to solve such problems with the conventional technologies and provide an organic thin-film light-emitting device that has improved luminous efficiency and durable life.

The present invention includes a light-emitting device material including a carbazole dimer skeleton-containing compound represented by the following general formula (1).

[Chemical Formula 1]

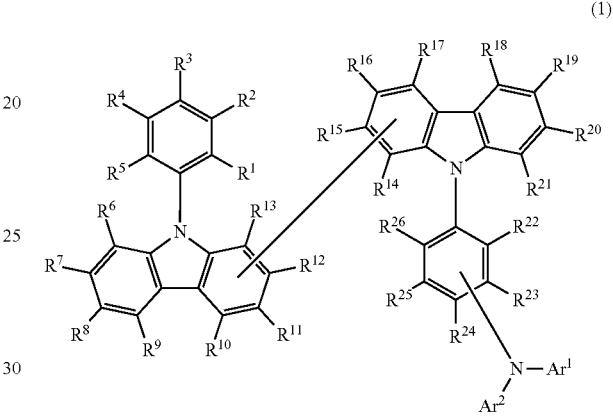

(1)

wherein $R^1$ to $R^{21}$ may be the same or different and are each selected from the group consisting of hydrogen, an alkyl group, a cycloalkyl group, a heterocyclic group, an alkenyl group, a cycloalkenyl group, an alkynyl group, a halogen, a carbonyl group, a carboxyl group, an oxycarbonyl group, a carbamoyl group, a silyl group and —P(=O)$R^{27}R^{28}$, wherein $R^{27}$ and $R^{28}$ are each an aryl group or a heteroaryl group, with the proviso that two carbazole skeletons are coupled at one of $R^6$ to $R^{13}$ and one of $R^{14}$ to $R^{21}$; and $R^{22}$ to $R^{26}$ satisfy any of the following requirements (A) and (B):

(A) at least one of $R^{23}$ and $R^{25}$ is $NAr^1Ar^2$, others may be the same or different and are each selected from the group consisting of hydrogen, an alkyl group, a cycloalkyl group, a heterocyclic group, an alkenyl group, a cycloalkenyl group, an alkynyl group, a halogen, a carbonyl group, a carboxyl group, an oxycarbonyl group, a carbamoyl group, a silyl group and —P(=O)$R^{27}R^{28}$ and $Ar^1$ and $Ar^2$ may be the same or different and each represent a substituted or unsubstituted phenyl group; and (B) $R^{24}$ is $NAr^1Ar^2$, others may be the same or different and are each selected from the group consisting of hydrogen, an alkyl group, a cycloalkyl group, a heterocyclic group, an alkenyl group, a cycloalkenyl group, an alkynyl group, a halogen, a carbonyl group, a carboxyl group, an oxycarbonyl group, a carbamoyl group, a silyl group and —P(=O)$R^{27}R^{28}$, and $Ar^1$ and $Ar^2$ may be the same or different, and each represent an unsubstituted phenyl group, a phenyl group substituted with an alkyl group, a phenyl group substituted with a halogen, or a phenyl group substituted with a phenyl group, with the proviso that $Ar^1$ and $Ar^2$ do not represent a phenyl group substituted with a phenyl group at the same time.

According to the present invention, there can be provided an organic electric field light-emitting device having high luminous efficiency, and further having sufficient durable life.

DETAILED DESCRIPTION OF EMBODIMENTS OF THE INVENTION

The compound represented by the general formula (1) in the present invention is described in detail below.

[Chemical Formula 2]

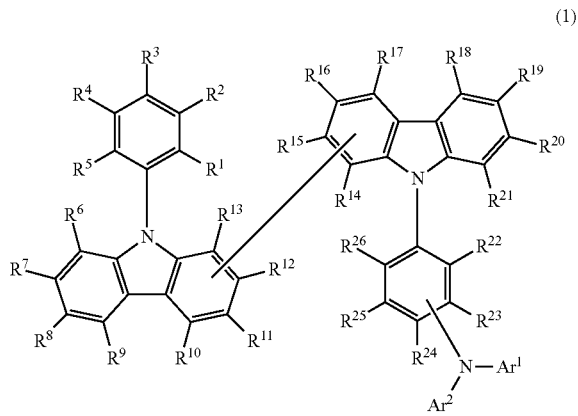

(1)

wherein $R^1$ to $R^{21}$ may be the same or different and are each selected from the group consisting of hydrogen, an alkyl group, a cycloalkyl group, a heterocyclic group, an alkenyl group, a cycloalkenyl group, an alkynyl group, a halogen, a carbonyl group, a carboxyl group, an oxycarbonyl group, a carbamoyl group, a silyl group and —P(=O)$R^{27}R^{28}$, wherein $R^{27}$ and $R^{28}$ are each an aryl group or a heteroaryl group, with the proviso that two carbazole skeletons are coupled at one of $R^6$ to $R^{13}$ and one of $R^{14}$ to $R^{21}$; and $R^{22}$ to $R^{26}$ satisfy any of the following requirements (A) and (B):

(A) at least one of $R^{23}$ and $R^{25}$ is $NAr^1Ar^2$, others may be the same or different and are each selected from the group consisting of hydrogen, an alkyl group, a cycloalkyl group, a heterocyclic group, an alkenyl group, a cycloalkenyl group, an alkynyl group, a halogen, a carbonyl group, a carboxyl group, an oxycarbonyl group, a carbamoyl group, a silyl group and —P(=O)$R^{27}R^{28}$, and $Ar^1$ and $Ar^2$ may be the same or different and each represent a substituted or unsubstituted phenyl group; and (B) $R^{24}$ is $NAr^1Ar^2$, others may be the same or different and are each selected from the group consisting of hydrogen, an alkyl group, a cycloalkyl group, a heterocyclic group, an alkenyl group, a cycloalkenyl group, an alkynyl group, a halogen, a carbonyl group, a carboxyl group, an oxycarbonyl group, a carbamoyl group, a silyl group and —P(=O)$R^{27}R^{28}$, and $Ar^1$ and $Ar^2$ may be the same or different, and each represent an unsubstituted phenyl group, a phenyl group substituted with an alkyl group, a phenyl group substituted with a halogen, or a phenyl group substituted with a phenyl group, with the proviso that $Ar^1$ and $Ar^2$ do not represent a phenyl group substituted with a phenyl group at the same time.

Among these substituents, hydrogen may be heavy hydrogen. When an "unsubstituted phenyl group" etc. is mentioned, hydrogen contained in the phenyl group may be heavy hydrogen.

The alkyl group denotes a saturated aliphatic hydrocarbon group, such as a methyl group, an ethyl group, a n-propyl group, an isopropyl group, a n-butyl group, a sec-butyl group, or a tert-butyl group, and it may or may not have a substituent. The number of carbon atoms in the alkyl group is not particularly limited, but from the viewpoints of easy availability and cost, it is usually within the range of 1 or more and 20 or less, more preferably 1 or more and 8 or less.

The cycloalkyl group denotes a saturated alicyclic hydrocarbon group, such as cyclopropyl, cyclohexyl, norbornyl, and adamantyl, and this may or may not have a substituent. The number of carbon atoms in the alkyl group moiety is not particularly limited, but is usually within the range of 3 or more and 20 or less.

The heterocyclic group denotes an aliphatic ring having an atom other than carbon in the ring, such as a pyran ring, a piperidine ring, and a cyclic amide, and this may or may not have a substituent. The number of carbon atoms in the heterocyclic group is not particularly limited, but is usually within the range of 2 or more and 20 or less.

The alkenyl group denotes an unsaturated aliphatic hydrocarbon group containing a double bond, such as a vinyl group, an allyl group, and a butadienyl group, and this may or may not have a substituent. The number of carbon atoms in the alkenyl group is not particularly limited, but is usually within the range of 2 or more and 20 or less.

The cycloalkenyl group denotes an unsaturated alicyclic hydrocarbon group containing a double bond, such as a cyclopentenyl group, a cyclopentadienyl group, and a cyclohexenyl group, and this may or may not have a substituent. The number of carbon atoms of the cycloalkenyl group is not specifically limited, but is usually within the range of 2 or more and 20 or less.

The alkynyl group denotes an unsaturated aliphatic hydrocarbon group containing a triple bond, such as an ethynyl group, and this may or may not have a substituent. The number of carbon atoms in the alkynyl group is not particularly limited, but is usually within the range of 2 or more and 20 or less.

The halogen denotes fluorine, chlorine, bromine or iodine.

The carbonyl group, the carboxyl group, the oxycarbonyl group and the carbamoyl group may or may not have a substituent.

The silyl group denotes a functional group having a bond with a silicon atom, such as a trimethylsilyl group, and this may or may not have a substituent. The number of carbon atoms in the silyl group is not particularly limited, but is usually within the range of 3 or more and 20 or less. In addition, the number of silicon atoms is usually within the range of 1 or more and 6 or less.

—P(=O)$R^{27}R^{28}$ may or may not have a substituent.

The aryl group represents an aromatic hydrocarbon group, such as a phenyl group, a biphenyl group, a fluorenyl group, a phenanthryl group, a triphenylenyl group and a terphenyl group. The aryl group may or may not have a substituent. The number of carbon atoms in the aryl group is not particularly limited, but is usually within the range of 6 or more and 40 or less.

The heteroaryl group denotes a cyclic aromatic group having one or a plurality of atoms other than carbon in the ring, such as a furanyl group, a thiophenyl group, a pyridyl group, a pyrazinyl group, a pyrimidinyl group, a triazinyl group, a benzofuranyl group, a benzothiophenyl group and an indolyl group, and this may be unsubstituted or substituted. The number of carbon atoms in the heteroaryl group is not particularly limited, but is usually within the range of 2 or more and 30 or less.

Conventional compounds having a carbazole skeleton do not necessarily have sufficient performance as a light-emitting device material. For example, 9,9'-diphenyl-9H, 9'H-3, 3'-bicarbazole and 1,3-di(9H-carbazol-9-yl)benzene (abbreviated name: mCP) are materials that have high triplet energy and are generally used as an exciton blocking material, but they have the problem that the driving voltage increases because the ionization potential is high and hole injecting and transporting properties are not satisfactory.

In studies on improvement thereof, the present inventors focused on a high hole transporting ability and high triplet energy of a carbazole skeleton-containing compound. Generally, the carbazole skeleton-containing compound has a property to transport charges of both a hole and an electron. The present inventors conceived that the conventional carbazole skeleton-containing compound has a low hole transporting ability, and therefore the ratio of holes entering an emissive layer is lower than that of electrons entering from an electron transporting layer, so that the balance of charges in the emissive layer is lost, leading to deterioration of device performance. Thus, when carbazole is dimerized, conjugation is expanded to improve the hole transporting property. However, some substituents on the nitrogen atom may hinder the hole transporting ability, and all carbazole dimers do not necessarily have a high hole transporting ability. Here, when a triarylamine skeleton which has exhibited excellent properties as a hole transporting substituent heretofore is present as a substituent on the nitrogen atom in the carbazole dimer, a higher hole transporting property can be provided. For the aryl group in the skeleton, however, it has become apparent that the same effect is not obtained for all aryl groups. For example, it has become apparent that the naphthyl group of the compound 33 or compound 36 (having the structure shown below) in KR 2010-0079458 A itself has low triplet energy, so that triplet energy of the compound is reduced. When an device is prepared using a compound having low triplet energy as an exciton blocking material, luminous efficiency is deteriorated by excitons leaked from an emissive layer, and therefore a compound having higher triplet energy is preferred.

[Chemical Formula 3]

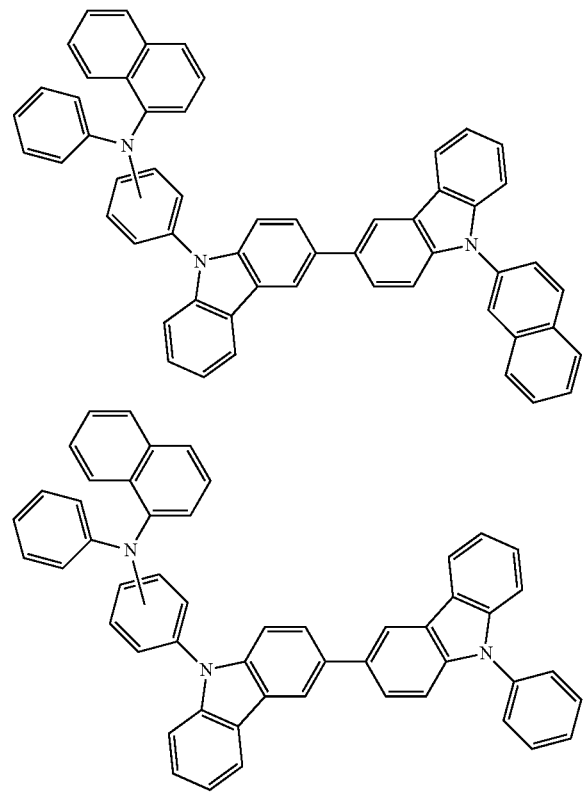

On the other hand, in a compound having a substituent at the ortho position in the carbazole dimer like the compound shown in Table 1 in WO 2006/61759 A, molecules are twisted, so that conjugation is not expanded even though carbazole is dimerized, and therefore triplet energy of carbazole itself can be maintained, and the value of triplet energy as a compound is also high. However, as described above, conjugation is not expanded, and therefore an effect of enhancing the hole transporting property is not obtained.

As described above, maintenance of high triplet energy and exhibition of a high hole transporting property is in the relationship of trade-off, and a material capable of achieving both the former and the latter has not been found. The present inventors have conducted vigorous studies, and resultantly found that a compound having a triarylamine skeleton, particularly a triphenylamine skeleton, as a substituent on the nitrogen atom and represented by the general formula (1) has a high hole transporting property while maintaining high triplet energy, leading to the present invention.

Preferably, the compound represented by the general formula (1) contains 2 carbazole skeletons per molecule, thereby providing a high thin film stability and an excellent heat resistance. When 3 or more carbazole skeletons are contained, there is the concern of thermal decomposition, and therefore the number of carbazole skeletons is preferably 2. Two carbazole skeletons are directly coupled.

The compound represented by the general formula (1) exhibits an excellent hole transporting ability because a substituent on one nitrogen atom has a triphenylamine skeleton. When both of substituents on two nitrogen atoms have a triphenylamine skeleton, the molecular weight becomes 800 or more, so that the sublimation temperature and the vapor deposition temperature are increased. Generally, when an organic material is deposited, it is deposited at a high temperature for a long period of time, and therefore it is desirable that there be a large difference between the deposition temperature and the sublimation temperature. If the molecular weight of the compound represented by the general formula (1) is so large that deposition must be performed at a high temperature, a heat load applied to the compound itself increases, so that a part of the compound may be decomposed and deposited. There is a possibility that ingress of such a decomposition product significantly affects the characteristics, particularly the life, of the device. For reducing the possibility, a molecular weight of 750 or less is desirable, and a molecular weight of 730 or less is more preferable because the margin of the sublimation temperature is widened. The molecular weight is further preferably 725 or less, especially preferably 700 or less. Therefore, the compound represented by the general formula (1) is preferably a compound in which only a substituent on one nitrogen atom has a triphenylamine skeleton.

For the substituent having a triphenylamine skeleton, two aspects may be presented. In one embodiment (A), at least one of $R^{23}$ and $R^{25}$ is $NAr^1Ar^2$, others may be the same or different and are each selected from the group consisting of hydrogen, an alkyl group, a cycloalkyl group, a heterocyclic group, an alkenyl group, a cycloalkenyl group, an alkynyl group, a halogen, a carbonyl group, a carboxyl group, an oxycarbonyl group, a carbamoyl group, a silyl group and —P(=O)$R^{27}R^{28}$, and $Ar^1$ and $Ar^2$ may be the same or different and each represent a substituted or unsubstituted phenyl group.

Since at least one of $R^{23}$ and $R^{25}$ is $NAr^1Ar^2$, asymmetry of the molecule is further increased, so that a stable thin film can be formed, leading to enhancement of durability. Particularly preferably, one of $R^{23}$ and $R^{25}$ is $NAr^1Ar^2$.

$Ar^1$ and $Ar^2$ in the embodiment (A) are each a substituted or unsubstituted phenyl group, the substituent group in this case is preferably an aryl group, an alkyl group or a halogen. The aryl group slightly expands conjugation, and therefore has an effect of slightly reducing the triplet level, but has an effect of stabilizing a cation as compared to an unsubstituted phenyl group, so that stabilization of the compound is increased. When stabilization of the compound is increased, degradation of the compound itself can be suppressed, and durability can be improved. The alkyl group and the halogen have almost no influence on conjugation, so that high triplet energy can be maintained.

In another embodiment (B), $R^{24}$ is $NAr^1Ar^2$, others may be the same or different and are each selected from the group consisting of hydrogen, an alkyl group, a cycloalkyl group, a heterocyclic group, an alkenyl group, a cycloalkenyl group, an alkynyl group, a halogen, a carbonyl group, a carboxyl group, an oxycarbonyl group, a carbamoyl group, a silyl group and —P(=O)$R^{27}R^{28}$, and $Ar^1$ and $Ar^2$ may be the same or different, and each represent an unsubstituted phenyl group, a phenyl group substituted with an alkyl group, a phenyl group substituted with a halogen, or a phenyl group substituted with a phenyl group, with the proviso that $Ar^1$ and $Ar^2$ do not represent a phenyl group substituted with a phenyl group at the same time.

Since $R^{24}$ is $NAr^1Ar^2$ and $Ar^1$ and $Ar^2$ are selected as described above, the ionization potential decreases, and hole injecting and transporting properties are improved, so that the driving voltage can be reduced. Further, the hole injecting property is improved, and therefore the rate of holes entering the adjacent emissive layer is increased, so that the probability of recombination with electrons in the emissive layer is increased, resulting in enhancement of luminous efficiency. Since one of $Ar^1$ and $Ar^2$ is an unsubstituted phenyl group, and the other is a phenyl group substituted with an alkyl group, a phenyl group substituted with a halogen, or a phenyl group substituted with a phenyl group, asymmetry of the molecule is further increased, so that a stable thin film can be formed, leading to enhancement of durability. Further, an effect of stabilizing a cation is provided, and therefore stabilization of the compound is increased. When stabilization of the compound is increased, degradation of the compound itself can be suppressed, and durability can be improved. The alkyl group and the halogen have almost no influence on conjugation, so that high triplet energy can be maintained.

When the compound represented by the general formula (1) is used for a hole transporting layer, the hole transporting layer is in direct contact with an emissive layer containing a triplet emitter dopant, leakage of triplet excitation energy from the emissive layer occurs to reduce luminous efficiency if the triplet energy of the hole transporting layer is low. Particularly when the hole transporting layer is in direct contact with an emissive layer containing a green emitter dopant, leakage of triplet excitation energy from the emissive layer can be suppressed, so that the effect of enhancing luminous efficiency and increasing the life of a light-emitting device can be enhanced, if the triplet energy of the hole transporting layer is higher than the triplet energy of the emitter dopant. From such a viewpoint, the triplet energy of the compound represented by the general formula (1) is preferably 2.60 eV or more, further preferably 2.65 eV, especially preferably 2.70 eV or more. The upper limit is not particularly limited, but is preferably 3.10 eV or less.

The triplet energy in the present invention is a value determined from a phosphorescence spectrum. One example of a specific measurement method will be shown below. An organic material is dissolved in an appropriated solvent (sample: 10 μmol/l) to provide a phosphorescence measuring sample. The sample placed in a quartz cell is cooled to 77 K, and irradiated with excitation light, and a phosphorescence is measured. tangential line is drawn to a rise of the phosphorescence spectrum, the wavelength value is converted into an energy value, and the value thus obtained is defined as T1. One example of the measurement apparatus is Fluorescence Phosphorescence Spectrophotometer Fluoromax-4P manufactured by HORIBA, Ltd. and optional equipment for low temperature measurement. The measurement apparatus is not limited thereto, and measurement may be performed by combining a cooler and a container for low temperature with an excitation light source and a light receiving apparatus.

It is preferred that the compound represented by the general formula (1) is in the form of a compound represented by the general formula (2) because it has a part similar to a benzidine skeleton, so that the hole transporting ability can be further enhanced. Further, in the compound represented by the general formula (2), the molecule has an asymmetric structure with the substituents on the nitrogen atoms of two carbazole skeletons being different groups, and therefore the effect of suppressing an interaction of carbazole skeletons is enhanced, so that a stable thin film can be formed, leading to enhancement of durability.

[Chemical Formula 4]

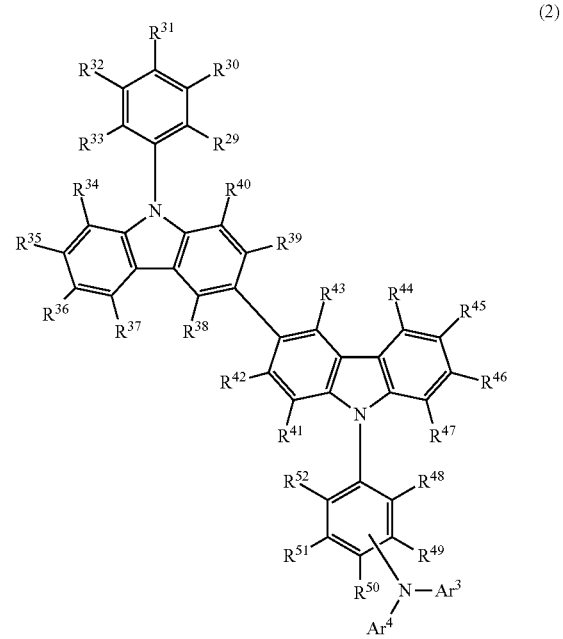

(2)

wherein $R^{29}$ to $R^{47}$ may be the same or different and are each selected from the group consisting of hydrogen, an alkyl group, a cycloalkyl group, a heterocyclic group, an alkenyl group, a cycloalkenyl group, an alkynyl group, a halogen, a carbonyl group, a carboxyl group, an oxycarbonyl group, a carbamoyl group, a silyl group and —P(=O)$R^{53}R^{54}$, wherein $R^{53}$ and $R^{54}$ are each an aryl group or a heteroaryl group, $R^{48}$ to $R^{52}$ satisfy any of the following requirements (A') and (B'):

(A') at least one of $R^{49}$ and $R^{51}$ is $NAr^3Ar^4$, others may be the same or different and are each selected from the group consisting of hydrogen, an alkyl group, a cycloalkyl group, a heterocyclic group, an alkenyl group, a cycloalkenyl group, an alkynyl group, a halogen, a carbonyl group, a carboxyl group, an oxycarbonyl group, a carbamoyl group, a silyl group and —P(=O)$R^{53}R^{54}$, and $Ar^3$ and $Ar^4$ may be the same or different and each represent a substituted or unsubstituted phenyl group; and (B') at least one of $R^{49}$ and $R^{51}$ is $NAr^3Ar^4$, others may be the same or different and are each selected from the group consisting of hydrogen, an alkyl group, a cycloalkyl group, a heterocyclic group, an alkenyl group, a cycloalkenyl group, an alkynyl group, a halogen, a carbonyl group, a carboxyl group, an oxycarbonyl group, a carbamoyl group, a silyl group and —P(=O)$R^{53}R^{54}$, and $Ar^3$ and $Ar^4$ may be the same or different, and each represent an unsubstituted phenyl group, a phenyl group substituted with an alkyl group, a phenyl group substituted with a halogen, or a phenyl group substituted with a phenyl group, with the proviso that $Ar^3$ and $Ar^4$ do not represent a phenyl group substituted with a phenyl group at the same time.

Descriptions of these substituents are similar to those for the above general formula (1).

Further, when the compound represented by the general formula (1) is a compound of the embodiment (A), wherein $Ar^1$ and $Ar^2$, and the compound represented by the general formula (2) is a compound of the embodiment (A), wherein $Ar^3$ and $Ar^4$ are each an unsubstituted phenyl group, a phenyl group substituted with a phenyl group, a phenyl group substituted with an alkyl group, or a phenyl group substituted with a halogen, high triplet energy can be maintained, and easy inactivation can be suppressed, so that high luminous efficiency is achieved. The phenyl group slightly expands conjugation, and therefore has an effect of slightly reducing the triplet level, but has an effect of stabilizing a cation as compared to an unsubstituted phenyl group, so that stabilization of the compound is increased. When stabilization of the compound is increased, degradation of the compound itself can be suppressed, and durability can be improved. The alkyl group and the halogen have almost no influence on conjugation, so that high triplet energy can be maintained.

Further, when the compound represented by the general formula (1) is a compound of the embodiment (A), wherein $R^1$ to $R^{21}$ are all hydrogen, and among $R^{22}$ to $R^{26}$, one of $R^{23}$ and $R^{25}$ is $NAr^1Ar^2$ and others are all hydrogen, stabilization of the compound is increased, degradation of the compound itself can be suppressed, and durability can be improved. Synthesis can be performed in a large quantity at low costs in terms of a synthesis process.

When the compound represented by the general formula (1) is a compound of the embodiment (B), wherein $R^1$ to $R^{21}$ are all hydrogen, and among $R^{22}$ to $R^{26}$, $R^{24}$ is $NAr^1Ar^2$ and others are all hydrogen, stabilization of the compound is increased, degradation of the compound itself can be suppressed, and durability can be improved. Synthesis can be performed in a large quantity at low costs in terms of a synthesis process.

Further, it is preferred that $Ar^1$ and $Ar^2$ are different from each other because asymmetry of the molecule itself is further increased due to asymmetry of triarylamine, so that a stable thin film can be formed, leading to enhancement of durability. The phrase "$Ar^1$ and $Ar^2$ are different from each other" means that a group represented by $Ar^1$ and a group represented by $Ar^2$ are not consistent with each other in terms of presence/absence of a substituent, a position and a type among others.

The compound represented by the above general formula (1) is not particularly limited, and specific examples include the compounds below. The compounds below are illustrative, and compounds other than those specified here are also suitably used as long as they are represented by the general formula (1).

Examples of the compound of the embodiment (A) include the following compounds.

[Chemical Formula 5]

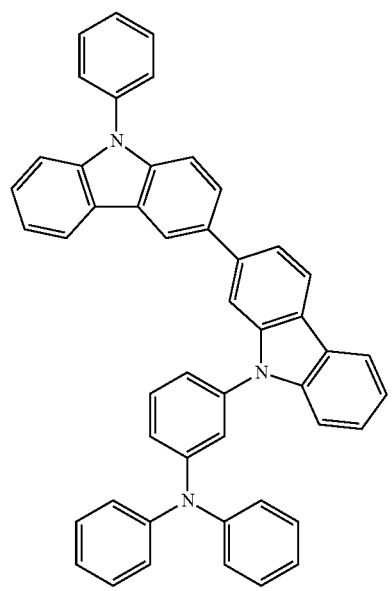

[1]

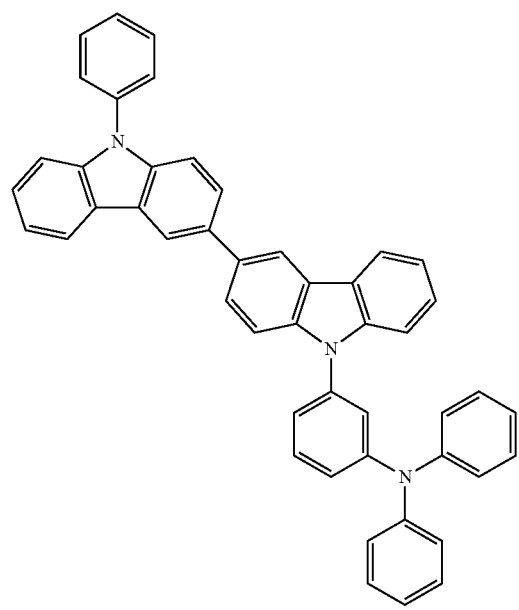

[2]

[3]
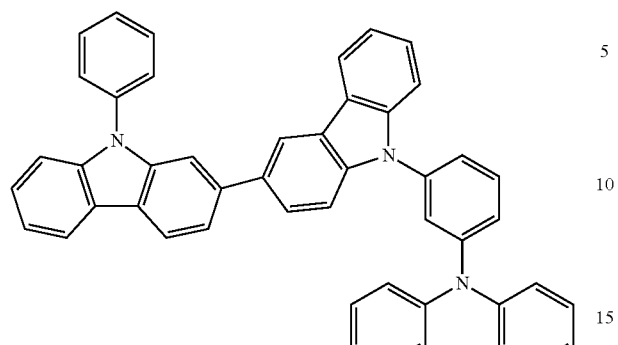
[4]
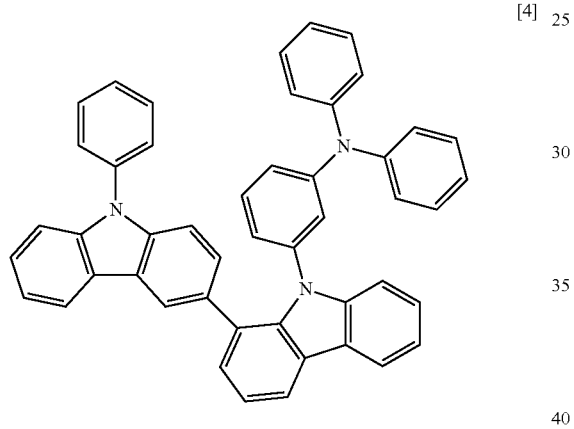
[5]
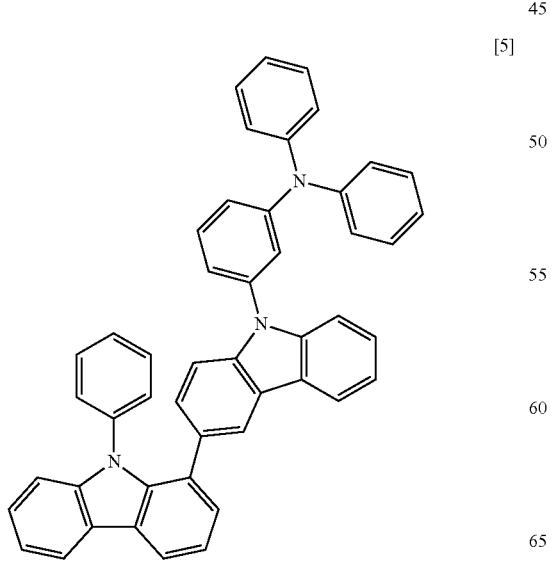
[6]
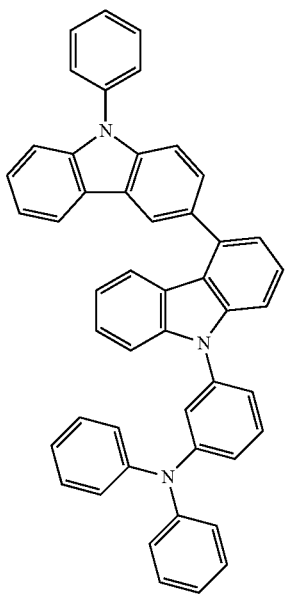
[7]
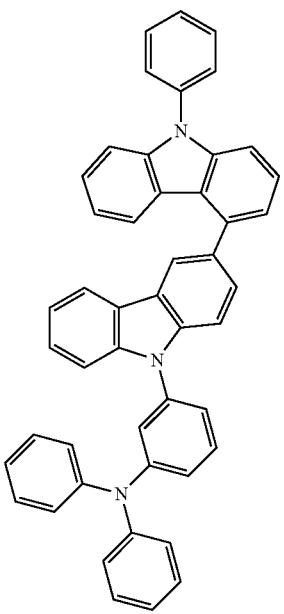

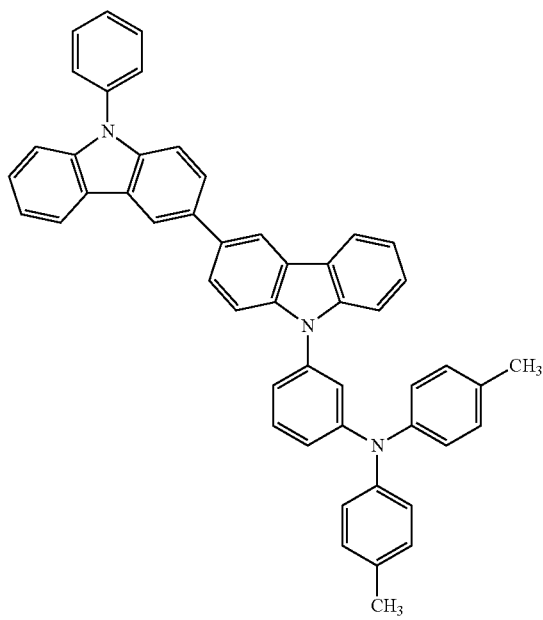
[8]
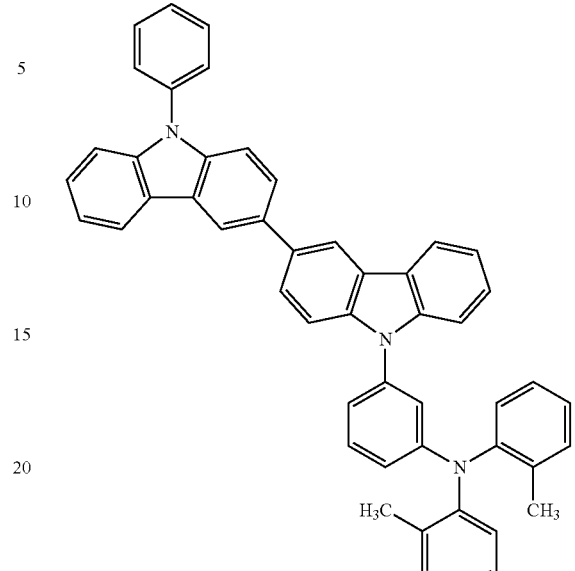
[10]
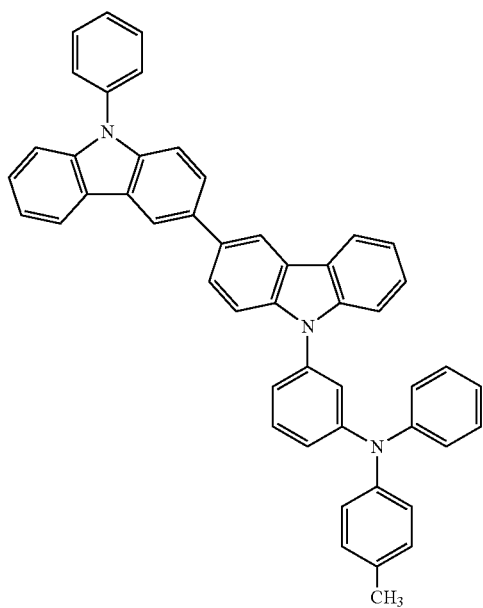
[9]
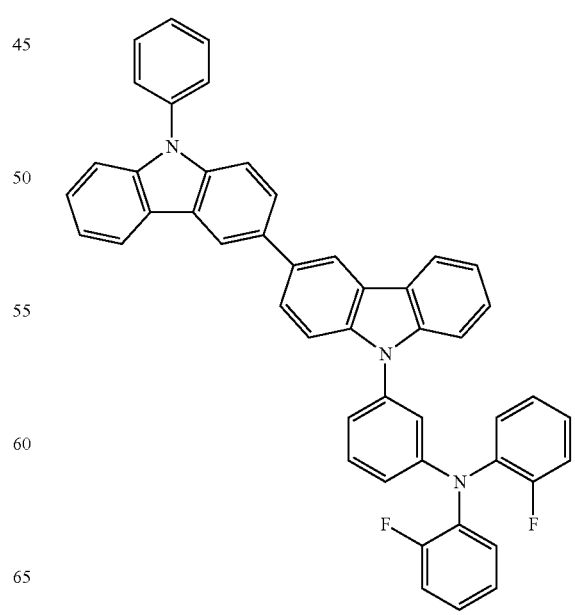
[11]

-continued
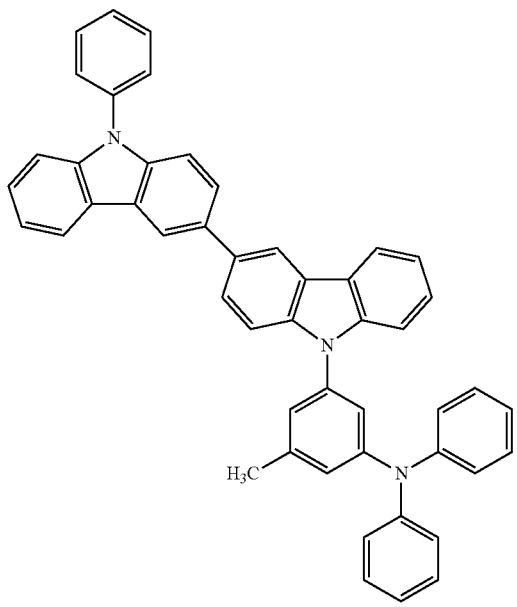
[12]
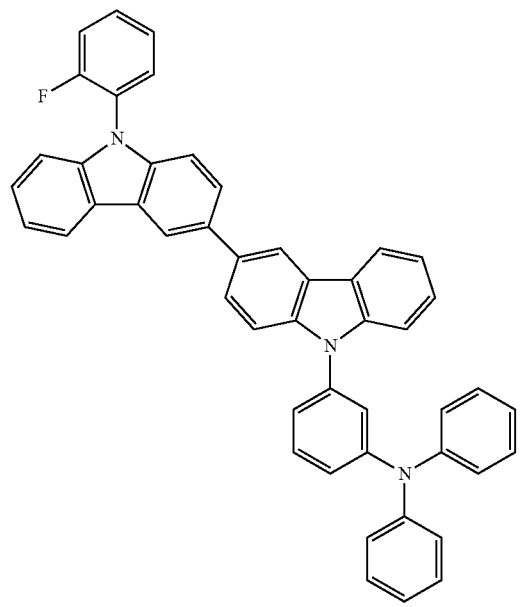
[26]
[Chemical Formula 6]
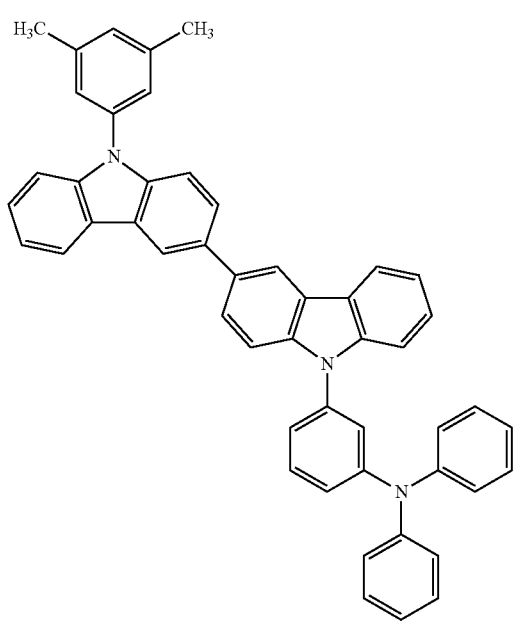
[25]
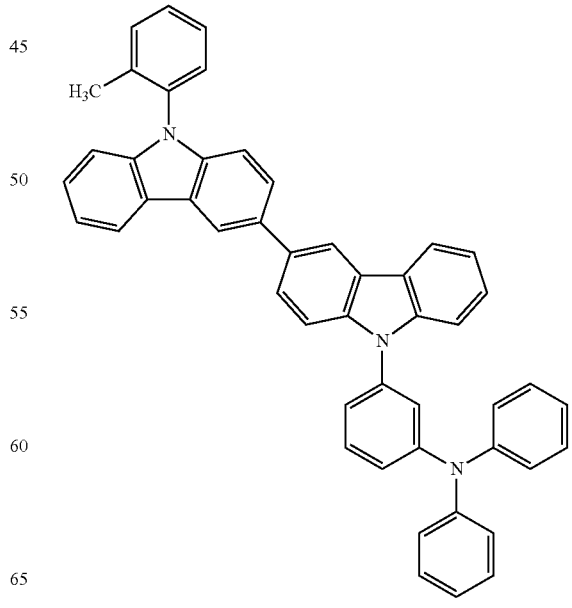
[27]

-continued
[28]
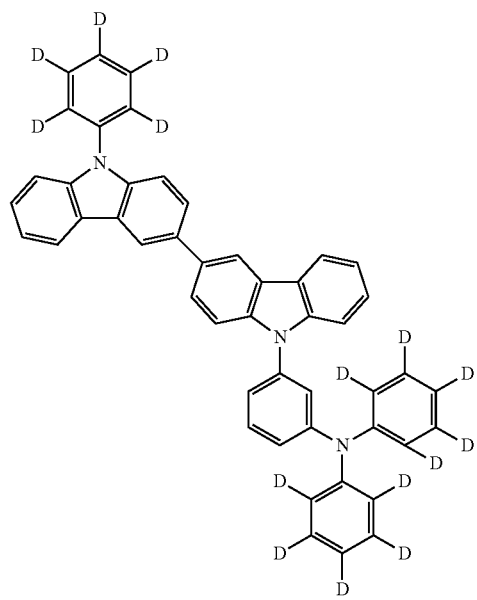
[30]
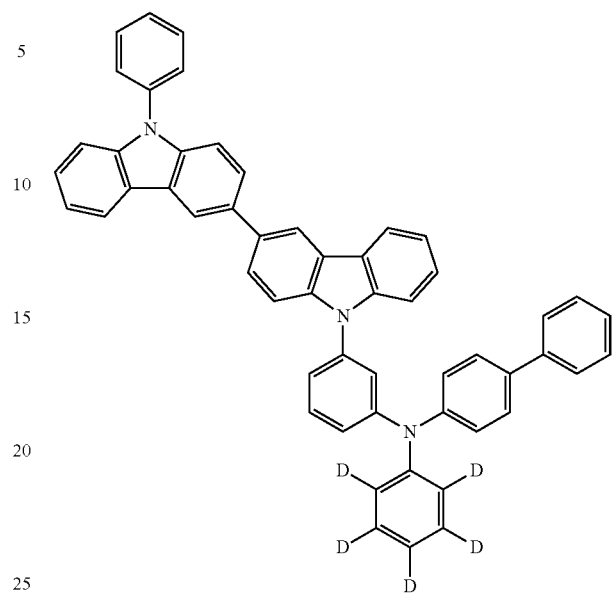
[29]
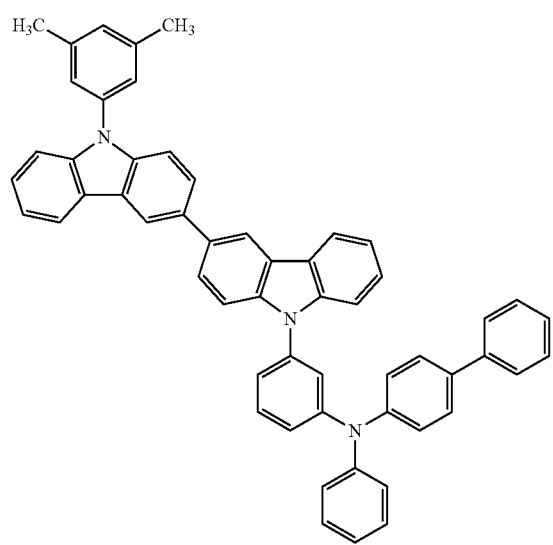
[31]
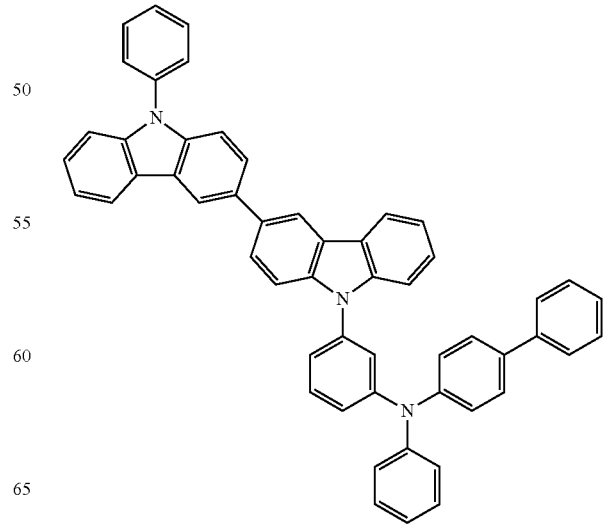

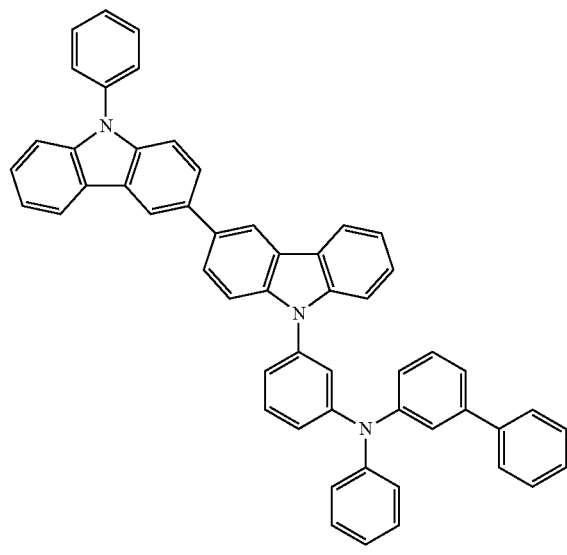
[32]
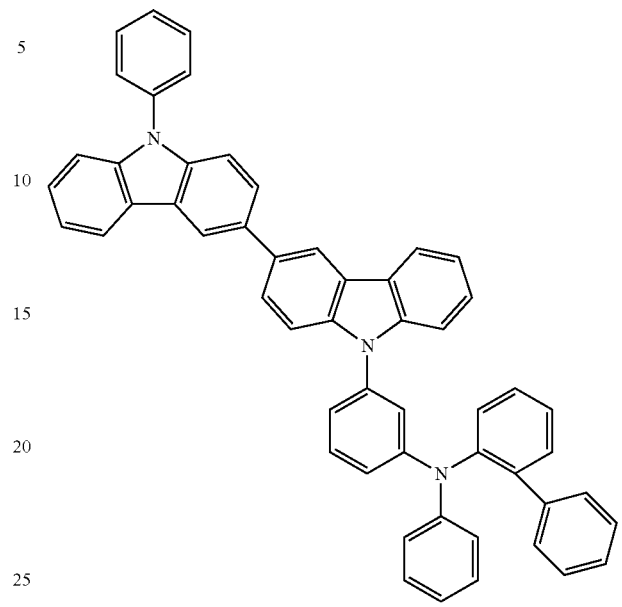
[34]
Examples of the compound of the embodiment (B) include the following compounds.
[Chemical Formula 7]
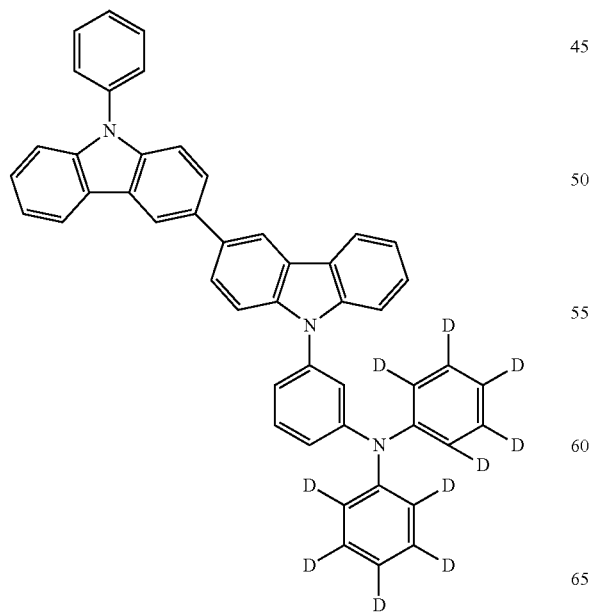
[33]
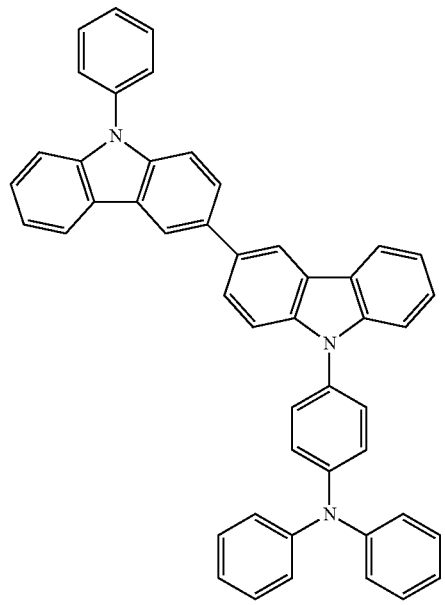
[35]

[36]
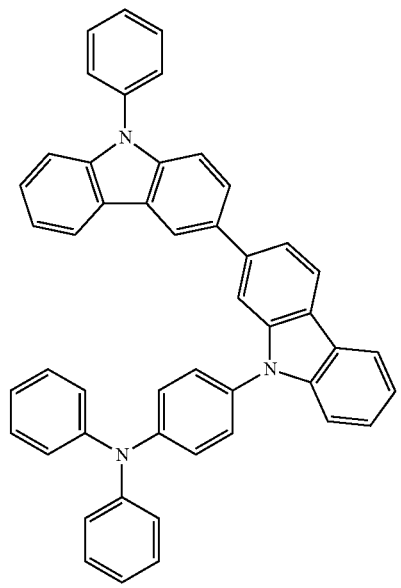
[37]
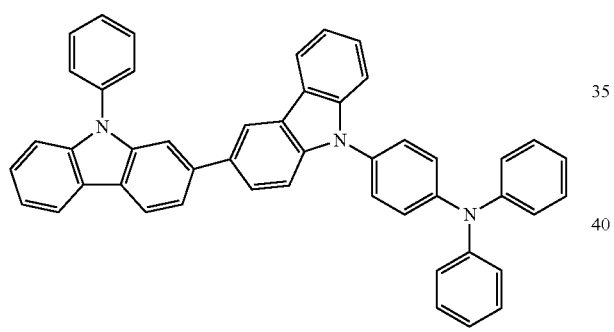
[38]
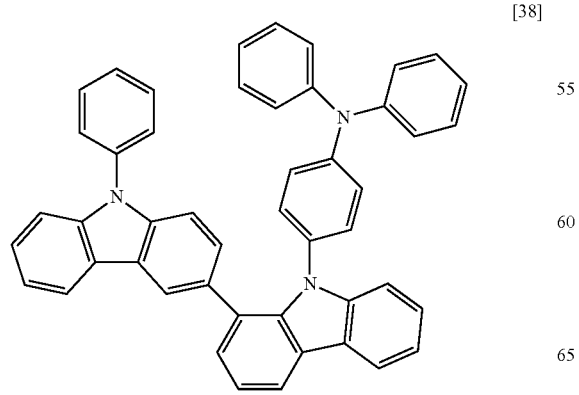
[39]
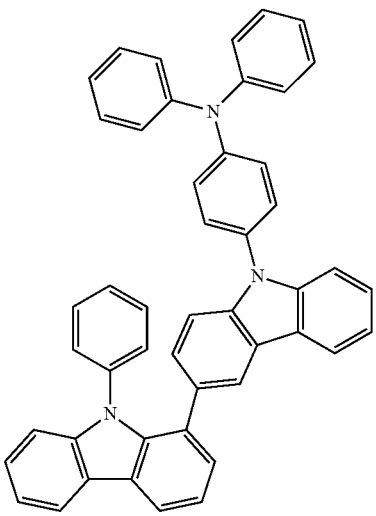
[40]
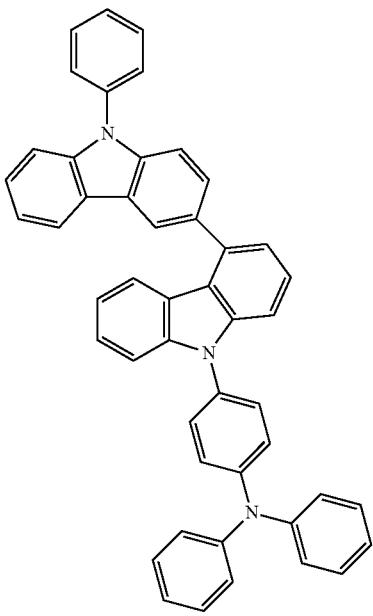

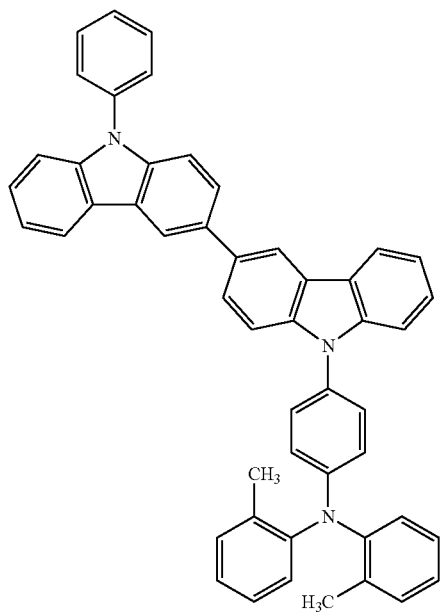
[41]
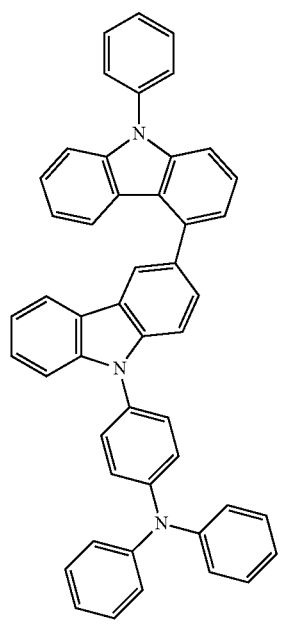
[42]
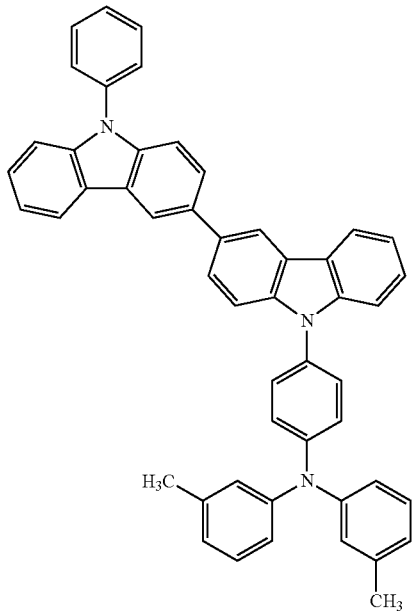
[43]
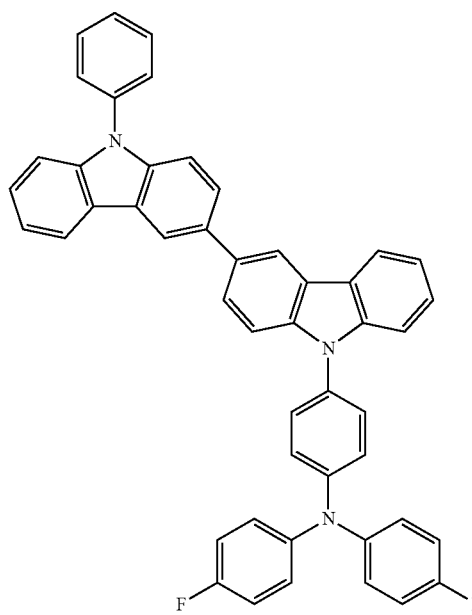
[44]

[Chemical Formula 8]
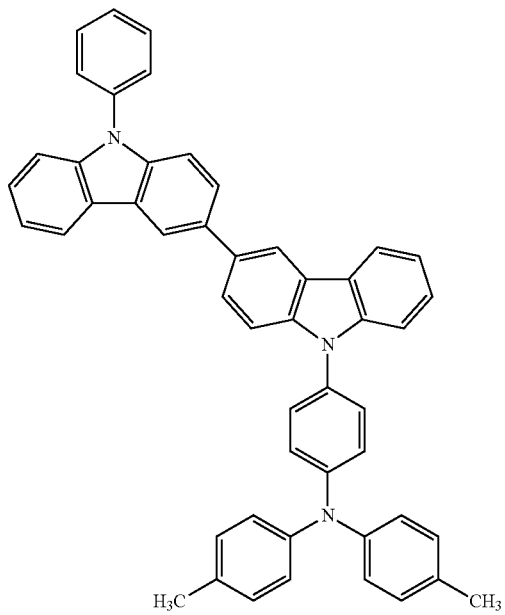
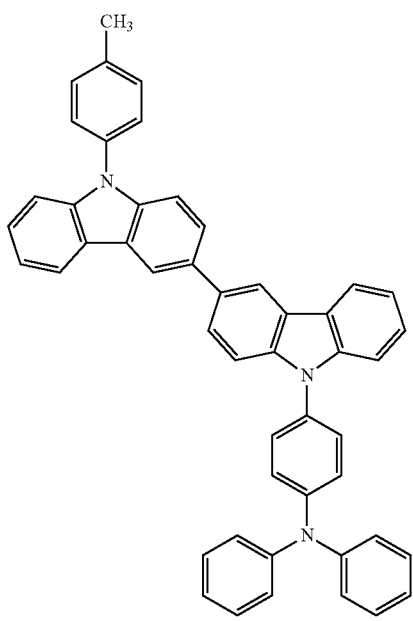
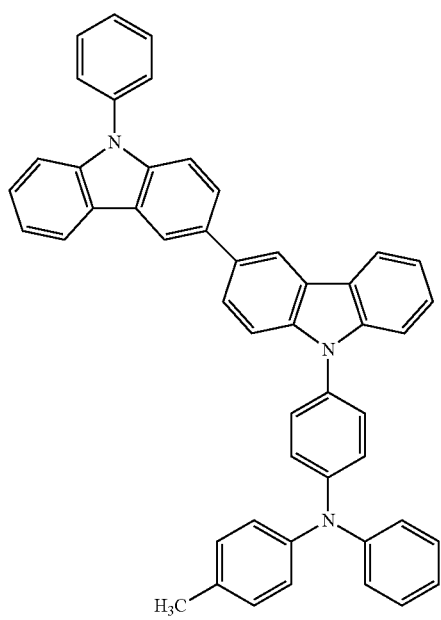
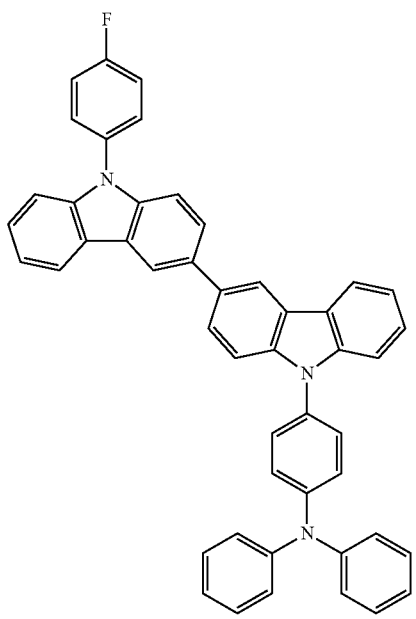

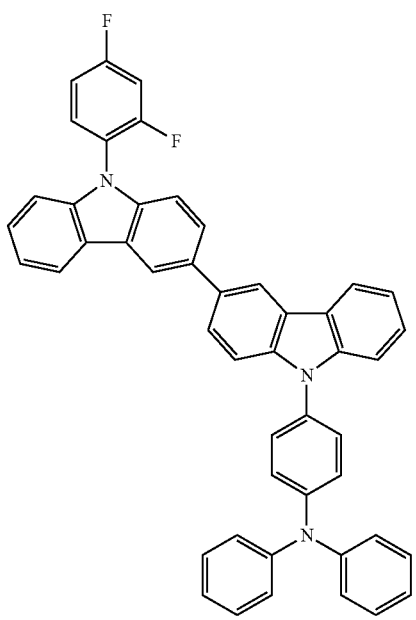
[49]
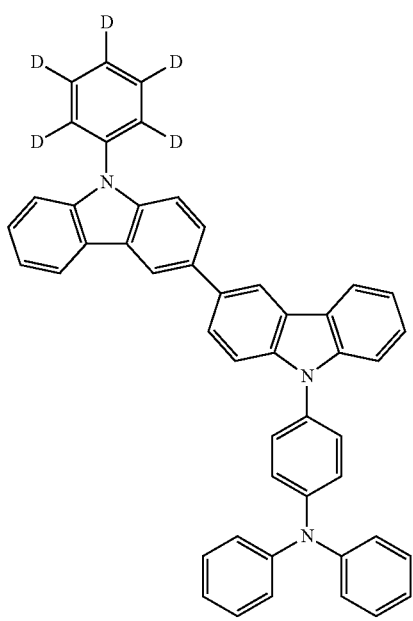
[51]
[50]
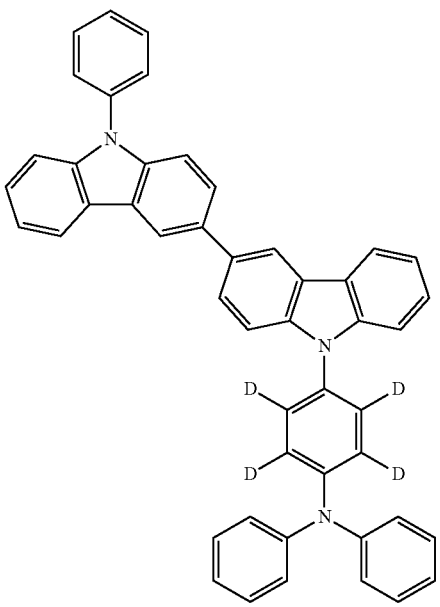
[52]

[53]
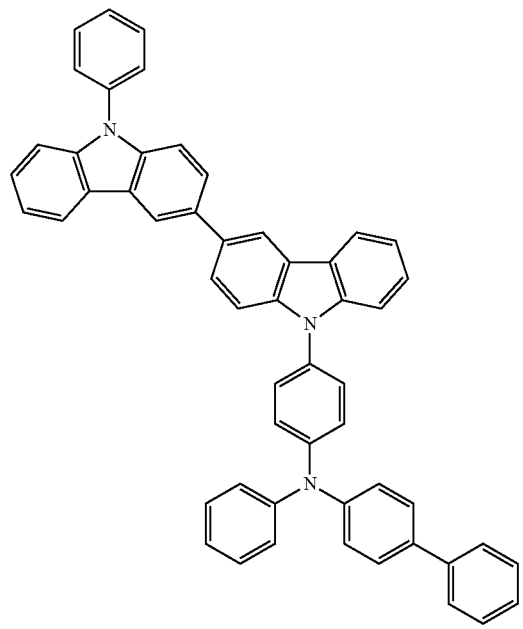
[55]
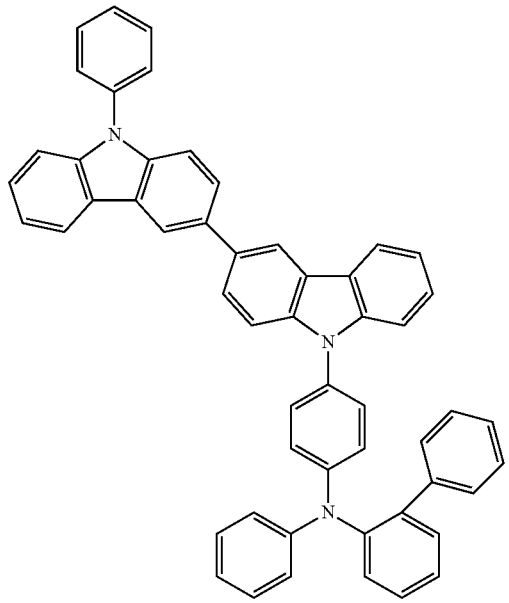
[54]
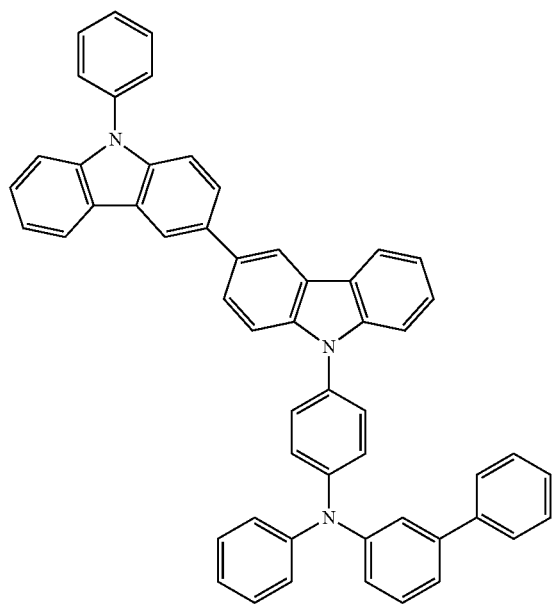
[56]
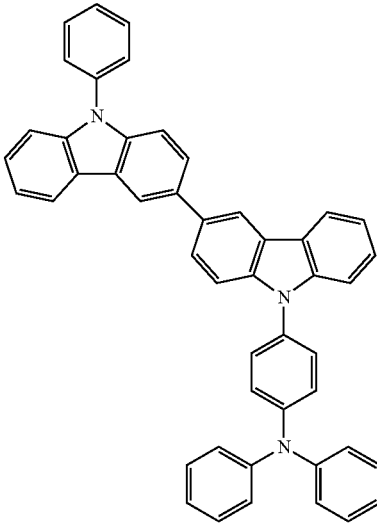

[57]

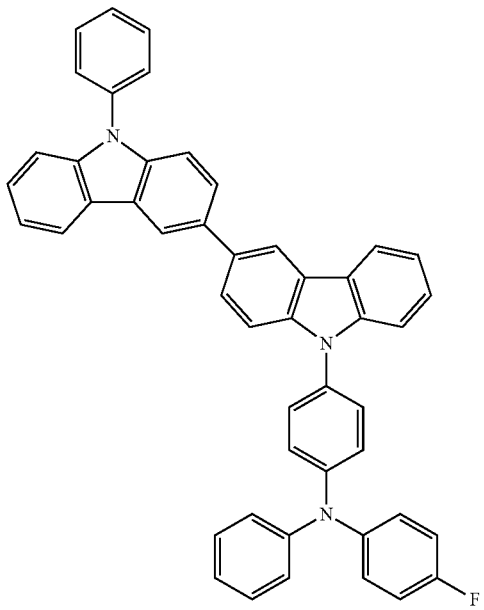

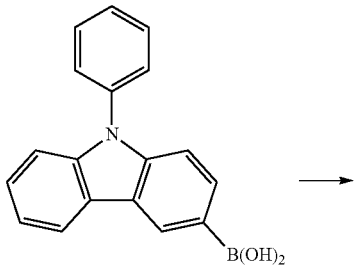

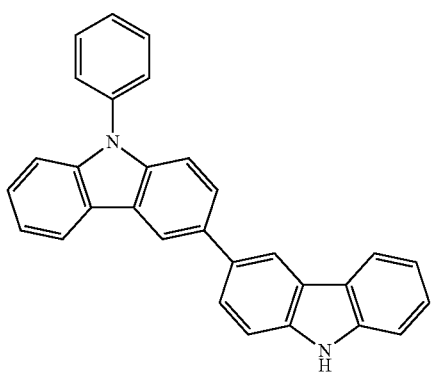

In the reaction described above, the reaction similarly proceeds even when 9-phenylcarbazole-2-boronic acid ester is used in place of 9-phenylcarbazole-3-boronic acid. In this case, a positional isomer of a carbazole dimer can be synthesized.

Examples of the method for introducing a substituent onto N of carbazole include, but are not limited thereto, a method using a coupling reaction of a carbazole derivative with a halide using a palladium or copper catalyst.

[Chemical Formula 10]

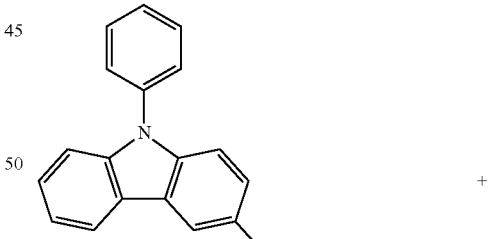

[58]

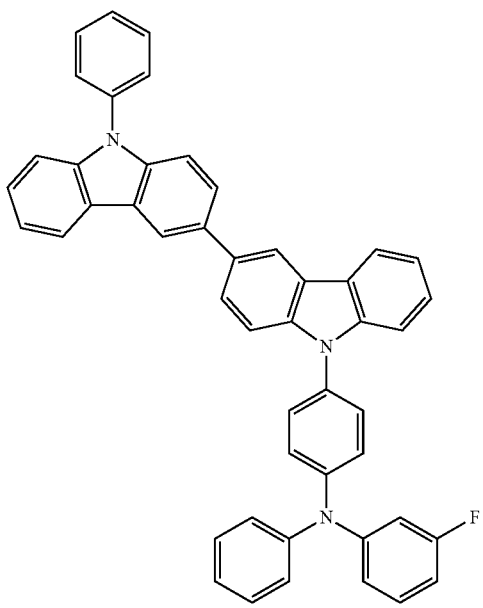

A known method can be used for synthesis of the carbazole skeleton-containing compound described above. Examples of the method for synthesizing a carbazole dimer include, but are not limited thereto, a method using a coupling reaction of a carbazole derivative with a halide or triflate using a palladium or copper catalyst. An example of using 9-phenylcarbazole-3-boronic acid is shown below as one example.

[Chemical Formula 9]

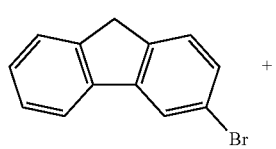

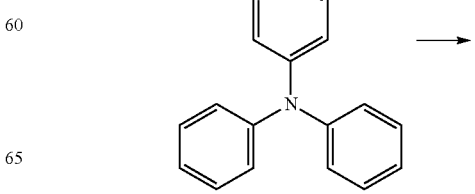

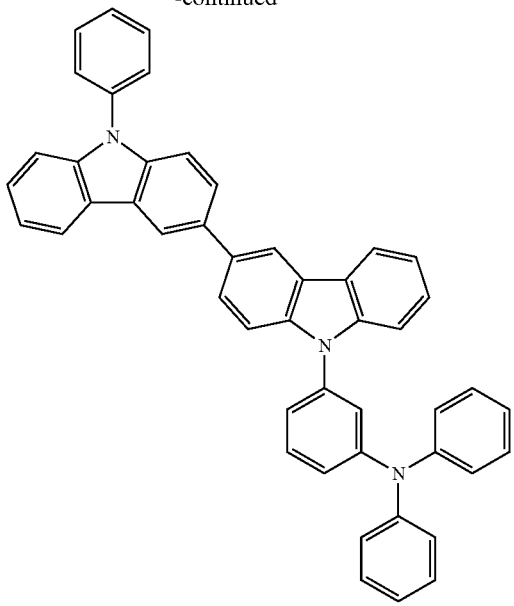

The compound represented by the general formula (1) is used as a light-emitting device material. Herein, the light-emitting device material in the present invention denotes a material to be used in any layer of a light-emitting device and also includes a material to be used in a protective film of a cathode, in addition to materials to be used in a hole injection layer, a hole transporting layer, an emissive layer and/or an electron transporting layer as described later. Use of the compound represented by the general formula (1) in the present invention in any layer of a light-emitting device can afford high luminous efficiency and also can afford a light-emitting device superior in durability.

Next, embodiments of the light-emitting device of the present invention will be described in detail. The light-emitting device has an anode and a cathode, and an organic layer interposed between the anode and the cathode, and the organic layer emits light by electric energy.

Examples of the layer configuration between the anode and the cathode in such a light-emitting device include, besides configurations made up of only an emissive layer, laminated configurations such as 1) emissive layer/electron transporting layer, 2) hole transporting layer/emissive layer, 3) hole transporting layer/emissive layer/electron transporting layer, 4) hole injection layer/hole transporting layer/emissive layer/electron transporting layer, 5) hole transporting layer/emissive layer/electron transporting layer/electron injection layer, and 6) hole injection layer/hole transporting layer/emissive layer/electron transporting layer/electron injection layer. Each of the layers may be in the form of a single layer or a plurality of layers, and may be doped.

While the compound represented by the general formula (1) can be used for any layer of the layers described above in a light-emitting device, it is particularly suitably used for a hole transporting layer.

In the light-emitting device, the anode and the cathode have a role for supplying a sufficient current for light emission of the device, and it is desirable that at least one of them is transparent or translucent in order to take out light. Usually, the anode formed on a substrate is made to be a transparent electrode.

While the material to be used for an anode is not particularly limited and may be electroconductive metal oxides, such as zinc oxide, tin oxide, indium oxide, tin oxide indium (ITO), and zinc-oxide indium (IZO), metals, such as gold, silver, and chromium, inorganic electroconductive substances, such as copper iodide and copper sulfide, electroconductive polymers, such as polythiophene, polypyrrole, and polyaniline as long as being a material that is capable of injecting holes into an organic layer efficiently and that is transparent or translucent in order to take out light, use of ITO glass or NESA glass is particularly desirable. These electrode materials may be used alone, or a plurality of materials may be used in lamination or in admixture. Since it is favorable that a sufficient current for light emission of the device can be supplied, the resistance of a transparent electrode is not limited, but from the viewpoint of the power consumption of the device, a low resistance is desirable. For example, an ITO substrate having a resistance of 300Ω/□ or lower functions as an device electrode, but since currently, it is possible to supply a substrate having a resistance of about 10Ω/□, it is particularly desirable to use a substrate having a low resistance of 20Ω/□ or lower. The thickness of ITO can be arbitrarily selected according to a resistance value, but ITO is usually used at a thickness of between 50 to 300 nm in many cases.

In addition, in order to retain the mechanical strength of the light-emitting device, it is preferred to form the light-emitting device on a substrate. As the substrate, a glass substrate such as soda glass or alkali-free glass is suitably used. Since it is favorable that the thickness of a glass substrate has a sufficient thickness for retaining the mechanical strength, a thickness of 0.5 mm or more is sufficient. Regarding the material of glass, since it is preferred that the amount of ions eluted from glass is low, alkali-free glass is more preferable. Alternatively, since soda lime glass provided with a barrier coating such as $SiO_2$ is commercially available, it can also be used. Further, as far as the first electrode stably functions, it is not necessary that the substrate is glass and, for example, the anode may be formed on a plastic substrate. Examples of a method of forming an ITO film include, but are not particularly limited to, an electron beam method, a sputtering method, and a chemical reaction method.

A material used in the cathode is not particularly limited, as far as it is a substance which can efficiently inject electrons into the emissive layer. Generally, metals such as platinum, gold, silver, copper, iron, tin, aluminum, and indium, or alloys or multilayer lamination of these metals with metals having a low work function such as lithium, sodium, potassium, calcium and magnesium are preferable. Among them, as a main component, aluminum, silver, and magnesium are preferable from the viewpoints of electric resistance value, easiness of making a film, stability of a film, and luminous efficiency. In particular, it is preferred that the material is constituted by magnesium and silver because electron injection into the electron transporting layer and the electron injection layer in the present invention becomes easy, and low voltage driving becomes possible.

Further, preferable examples include lamination of metals such as platinum, gold, silver, copper, iron, tin, aluminum, and indium, or alloys using these metals, inorganic substances such as silica, titania, and silicon nitride, and organic polymer compounds such as polyvinyl alcohol, polyvinyl chloride, and a hydrocarbon-based polymer compound as a protective film layer on the cathode for protecting the cathode. However, in the case of an device structure for taking out light from the cathode side (top emission structure), the protective film layer is selected from materials having light permeability in a visible light region. Examples of a method for preparation of these electrodes include, but are not particularly limited to, resistance heating, electron beam, sputtering, ion plating and coating.

The hole injection layer is a layer that is to be inserted to between an anode and a hole transporting layer. A single hole injection layer may be formed or, alternatively, a plurality of hole injection layers may be laminated. It is preferred that the hole injection layer is present between a hole transporting layer and an anode because this successfully results in lower voltage driving, increased durable life, and improvement in luminous efficiency due to improvement in the carrier balance of an device.

The material to be used for the hole injection layer is not particularly limited, and, for example, benzidine derivatives such as 4,4'-bis(N-(3-methylphenyl)-N-phenylamino)biphenyl (TPD), 4,4'-bis(N-(1-naphthyl)-N-phenylamino)biphenyl (NPD), 4,4'-bis(N,N-bis(4-biphenylyl)amino)biphenyl (TBDB) and bis(N,N'-diphenyl-4-aminophenyl)-N,N-diphenyl-4,4'-diamino-1,1'-biphenyl (TPD232); materials called starburst arylamines, such as 4,4',4''-tris(3-methylphenyl(phenyl)amino)triphenylamine (m-MTDATA) and 4,4',4''-tris(1-naphthyl(phenyl)amino)triphenylamine (1-TNATA); biscarbazole derivatives such as bis(N-arylcarbazole) or bis(N-alkylcarbazole); heterocyclic compounds such as pyrazoline derivatives, stilbene-based compounds, hydrazone-based compounds, benzofuran derivatives, thiophene derivatives, oxadiazole derivatives, phthalocyanine derivatives and porphyrin derivatives; and such polymers as polycarbonates and styrene derivatives having the aforementioned monomers on their side chains, polythiophene, polyaniline, polyfluorene, polyvinylcarbazole and polysilane are used. The compound represented by the general formula (1) may also be used. Especially, benzidine derivatives and starburst arylamine materials are more preferably used from the viewpoint of having a lower HOMO level than the compound represented by the general formula (1) and injecting and transporting holes smoothly from an anode to a hole transporting layer.

Such materials may be used alone, or alternatively two or more materials may be used in admixture. A hole injection layer may be formed by laminating a plurality of materials. Moreover, it is more preferable that the hole injection layer is formed of an acceptor material alone or the hole injection material described above is used with the material doped with an acceptor material because if so, the effects described above will be more remarkably obtained. The acceptor material is a material that forms a charge transfer complex with a hole transporting layer in contact therewith in the case where the compound is used in the form of a single layer film or forms a charge transfer complex with a material that constitutes a hole injection layer in the case where the compound is used while being doped into the material. Use of such a material improves the electrical conductivity of a hole injection layer and contributes more to drop the driving voltage of an device, thereby affording effects such as improvement in luminous efficiency and improvement in durable life.

Examples of the acceptor material include metal chlorides such as iron(III) chloride, aluminum chloride, gallium chloride, indium chloride, and antimony chloride, metal oxides such as molybdenum oxide, vanadium oxide, tungsten oxide, and ruthenium oxide, and charge transfer complexes such as tris(4-bromophenyl)aminium hexachloroantimonate (TBPAH). Moreover, organic compounds having a nitro group, a cyano group, halogen, or a trifluoromethyl group in the molecule, quinone-based compounds, acid anhydride-based compounds, and fullerene can also be used suitably. Specific examples of such compounds include hexacyanobutadiene, hexacyanobenzene, tetracyanoethylene, tetracyanoquinodimethane (TCNQ), tetrafluorotetracyanoquinodimethane (F4-TCNQ), radialene derivatives, p-fluoranil, p-chloranil, p-bromanil, p-benzoquinone, 2,6-dichlorobenzoquinone, 2,5-dichlorobenzoquinone, tetramethylbenzoquinone, 1,2,4,5-tetracyanobenzene, o-dicyanobenzene, p-dicyanobenzene, 1,4-dicyanotetrafluorobenzene, 2,3-dichloro-5,6-dicyanobenzoquinone, p-dinitrobenzene, m-dinitrobenzene, o-dinitrobenzene, p-cyanonitrobenzene, m-cyanonitrobenzene, o-cyanonitrobenzene, 1,4-naphthoquinone, 2,3-dichloronaphthoquinone, 1-nitronaphthalene, 2-nitronaphthalene, 1,3-dinitronaphthalene, 1,5-dinitronaphthalene, 9-cyanoanthracene, 9-nitroanthracene, 9,10-anthraquinone, 1,3,6,8-tetranitrocarbazole, 2,4,7-trinitro-9-fluorenone, 2,3,5,6-tetracyanopyridine, maleic anhydride, phthalic anhydride, C60, and C70.

Of these, metal oxides and cyano group-containing compounds are preferable because they can be easily handled and deposited and therefore the above-described effects can be obtained easily. In either of the case where a hole injection layer is formed of an acceptor material alone or the case where a hole injection layer is doped with an acceptor material, the hole injection layer may be a single layer or may be formed of a plurality of layers laminated.

The hole transporting layer is a layer that transports to an emissive layer holes injected from an anode. The hole transporting layer may be formed of either a single layer or a plurality of layers laminated.

The compound represented by the general formula (1) is preferably used for a hole injection layer and hole transporting layer of a light-emitting device because the compound has an ionization potential of 5.1 to 6.0 eV (value of a deposited film measured using AC-2 (manufactured by RIKEN KEIKI Co., Ltd.)), high triplet energy, high hole transporting property, and high film stability. The compound represented by the general formula (1) has a greater energy gap as compared to conventional hole transporting materials having a benzidine skeleton, and therefore has a high LUMO level and is excellent in electron blocking property. Moreover, it is preferred to use the compound represented by the general formula (1) as a hole transporting material of an device using a triplet emissive material. This is because the compound represented by the general formula (1) has high triplet energy and therefore does not cause the problem with conventional hole transporting materials having a benzidine skeleton that leak of triplet excitation energy occurs and luminous efficiency drops if the materials are in contact directly with an emissive layer containing a triplet emitter dopant because of the low triplet energy of the materials.

When being formed of a plurality of hole transporting layers, it is preferred that a hole transporting layer containing the compound represented by the general formula (1) is in contact with an emissive layer directly. This is because the compound represented by the general formula (1) has high electron blocking property and therefore can prevent the invasion of electrons flowing out of the emissive layer. Moreover, the compound represented by the general formula (1) has high triplet energy and therefore also has an effect of trapping the excitation energy of a triplet emissive material. Accordingly, it is preferred that a hole transporting layer containing the compound represented by the general formula (1) is indirect contact with an emissive layer also when a triplet emissive material is contained in the emissive layer.

The hole transporting layer may be formed of only the compound represented by formula (1) or alternatively may be incorporated with other materials as long as the effects of the present invention are not impaired. In this case, examples of other materials to be used include benzidine derivatives such as 4,4'-bis(N-(3-methylphenyl)-N-phenylamino)biphenyl (TPD), 4,4'-bis(N-(1-naphthyl)-N-phenylamino)biphenyl (NPD), 4,4'-bis(N,N-bis(4-biphenylyl)amino)biphenyl (TBDB) and bis(N,N'-diphenyl-4-aminophenyl)-N,N-diphenyl-4,4'-diamino-1,1'-biphenyl (TPD232); materials called starburst arylamines, such as 4,4',4''-tris(3-methylphenyl(phenyl)amino)triphenylamine (m-MTDATA) and 4,4',4''-tris(1-naphthyl(phenyl)amino)triphenylamine (1-TNATA); biscarbazole derivatives such as bis(N-arylcarbazole) or bis(N-alkylcarbazole); heterocyclic compounds such as pyrazoline derivatives, stilbene-based compounds, hydrazone-based compounds, benzofuran derivatives, thiophene derivatives, oxadiazole derivatives, phthalocyanine derivatives and porphyrin derivatives; and such polymers as polycarbonates and styrene derivatives having the aforementioned monomers on their side chains, polythiophene, polyaniline, polyfluorene, polyvinylcarbazole and polysilane.

The emissive layers may be in the form of a single layer or a plurality of layers, each of which is formed of an emissive material (host material, dopant material), and this may be a mixture of the host material and the dopant material, or the host material alone, or a mixture of two host materials and one dopant material. That is, in the preferred light-emitting device of the present invention, only the host material or the dopant material may emit light, or both of the host material and the dopant material emit light, in each emissive layer. From the viewpoints that electric energy is efficiently utilized, and light emission at high color purity is obtained, it is preferred that the emissive layer includes a mixture of the host material and the dopant material. In addition, the host material and the dopant material may be one kind or a combination of a plurality of kinds, respectively. The dopant material may be contained in a whole host material, or may be partially contained therein. The dopant material may be laminated, or may be dispersed. The dopant material can control an emitted color. When the amount of the dopant material is too large, concentration quenching occurs, and therefore the dopant material is used in an amount of preferably 30% by weight or less, further preferably 20% by weight or less based on the host material. As a doping method, the dopant material can be co-deposited with the host material, or the dopant material may be mixed with the host material in advance to be co-deposited simultaneously.

Besides the compound represented by the general formula (1), examples of the emissive material that can be used include, but are not particularly limited to, fused ring derivatives such as anthracene and pyrene, metal chelated oxinoid compounds including tris(8-quinolinolate)aluminum, bisstyryl derivatives such as bisstyrylanthracene derivatives and distyrylbenzene derivatives, tetraphenylbutadiene derivatives, indene derivatives, coumarin derivatives, oxadiazole derivatives, pyrrolopyridine derivatives, perinone derivatives, cyclopentadiene derivatives, oxadiazole derivatives, thiadiazolopyridine derivatives, dibenzofuran derivatives, carbazole derivatives, and indolocarbazole derivatives and, as a polymer series, polyphenylenevinylene derivatives, polyparaphenylene derivatives, and polythiophene derivatives, which have hitherto been known as a light emitting body.

The host material contained in the emissive material need not be restricted to only one type of compound, and a plurality of compounds of the present invention may be used in admixture or a compound of the present invention may be used in an admixture with one or more other host materials. Alternatively, those materials may be laminated. Examples of the host material which can be mixed include, but are not particularly limited to, compounds having a fused aryl ring such as naphthalene, anthracene, phenanthrene, pyrene, chrysene, naphthacene, triphenylene, perylene, fluoranthene, fluorene, and indene, and derivatives thereof, aromatic amine derivatives such as N,N'-dinaphthyl-N,N'-diphenyl-4,4'-diphenyl-1,1'-diamine, metal chelated oxinoid compounds including tris(8-quinolinato)aluminum (III), bisstyryl derivatives such as distyrylbenzene derivatives, tetraphenylbutadiene derivatives, indene derivatives, coumarin derivatives, oxadiazole derivatives, pyrrolopyridine derivatives, perinone derivatives, cyclopentadiene derivatives, pyrrolopyrrole derivatives, thiadiazolopyridine derivatives, dibenzofuran derivatives, carbazole derivatives, indolocarbazole derivatives and triazine derivatives and, as a polymer series, polyphenylenevinylene derivatives, polyparaphenylene derivatives, polyfluorene derivatives, polyvinylcarbazole derivatives, and polythiophene derivatives. Especially, metal chelated oxinoid compounds, dibenzofuran derivatives, dibenzothiophene derivatives, carbazole derivatives, indolocarbazole derivatives, triazine derivatives, triphenylene derivatives and the like are suitably used as a host which is used when the emissive layer performs triplet emission (phosphorescence emission).

The dopant material contained in the emissive material is not particularly limited, and examples thereof include compounds having an aryl ring, such as naphthalene, anthracene, phenanthrene, pyrene, triphenylene, perylene, fluorene and indene, or derivatives thereof (e.g. 2-(benzothiazole-2-yl)-9,10-diphenylanthracene, 5,6,11,12-tetraphenylnaphthacene and the like); compounds having a heteroaryl ring, such as furan, pyrrole, thiophene, silole, 9-silafluorene, 9,9'-spirobisilafluorene, benzothiophene, benzofuran, indole, dibenzothiophene, dibenzofuran, imidazopyridine, phenanthroline, pyrazine, naphthyridine, quinoxaline, pyrrolopyridine and thioxanthene, or derivatives thereof; distyrylbenzene derivatives; aminostyryl derivatives such as 4,4'-bis(2-(4-diphenylaminophenyl)ethenyl)biphenyl and 4,4'-bis(N-(stilbene-4-yl)-N-phenylamino)stilbene; aromatic acetylene derivatives; tetraphenylbutadiene derivatives; stilbene derivatives; aldazine derivatives; pyrromethene derivatives; diketopyrrolo[3,4-c]pyrrole derivatives; coumarin derivatives such as 2,3,5,6-1H,4H-tetrahydro-9-(2'-benzothiazolyl)quinolizino[9,9a,1-gh]coumarin; azole derivatives such as imidazole, thiazole, thiadiazole, carbazole, oxazole, oxadiazole and triazole, and metal complexes thereof; and aromatic amine derivatives represented by N,N'-diphenyl-N,N'-di(3-methylphenyl)-4,4'-diphenyl-1,1'-di amine.

In particular, the dopant to be used when an emissive layer is engaged in triplet light emission (emission of phosphorescence) is preferably a metal complex compound containing at least one metal selected from the group consisting of iridium (Ir), ruthenium (Ru), palladium (Pd), platinum (Pt), osmium (Os), and rhenium (Re). It is preferred that the ligand has a nitrogen-containing aromatic heterocyclic ring such as a phenylpyridine skeleton, a phenylquinoline skeleton or a carbene skeleton. However, the complex is not limited thereto, and a suitable complex is selected in context with an emitted color, a device performance and a host compound to be required. Specific examples thereof include a tris(2-phenylpyridyl) iridium complex, a tris{2-(2-thiophenyl)pyridyl}iridium complex, a tris{2-(2-benzothiophenyl)pyridyl}iridium complex, a tris(2-phenylbenzothiazole) iridium complex, a tris(2-phenylbenzoxazole) iridium complex, a trisbenzoquinoline iridium complex, a bis(2-phenyl pyridyl) (acetylacetonato) iridium complex, a bis{2-(2-thiophenyl)pyridyl}iridium complex, a bis{2-(2-benzothiophenyl)pyridyl}(acetylacetonato) iridium complex, a bis(2-phenylbenzothiazole)(acetylacetonato) iridium complex, a bis (2-phenylbenzoxazole)(acetylacetonato) iridium complex, a bisbenzoquinoline(acetylacetonato)iridium complex, a bis{2-(2,4-difluorophenyl)pyridyl}(acetylacetonato) iridium complex, a tetraethylporphyrin platinum complex, a {tris(thenoyltrifluoroacetone)-mono(1,10-phenanthroline)}europium complex, a {tris(thenoyltrifluoroacetone)-mono(4,7-diphenyl-1,10-phenanthroline)}europium complex, a {tris(1,3-diphenyl-1,3-propanedione)-mono(1,10-phenanthroline)}europium complex, and a trisacetylacetone terbium complex. Moreover, a phosphorescence dopant disclosed in JP 2009-130141 A is also used suitably. Although not limited to these, an iridium complex or a platinum complex is used preferably because highly efficient light can be obtained easily.

Regarding the above-described triplet emissive materials to be used as a dopant material, only one material may be contained in an emissive layer or, alternatively, two or more materials may be used in admixture. When two or more triplet emissive materials are used, the total weight of the dopant materials is preferably 30% by weight or less, further preferably 20% by weight or less based on the host material.

The emissive layer may further contain a third component for adjusting the carrier balance in the emissive layer or for stabilizing the layer structure of the emissive layer in addition to the above-described host material and the triplet emissive material. A material that does not cause interaction between a host material made of the carbazole skeleton-containing compound represented by the general formula (1) and a dopant material made of a triplet emissive material is selected as the third component.

Preferable host and dopant in a triplet emission system are not particularly limited, and specific examples thereof include the following.

[Chemical Formula 11]

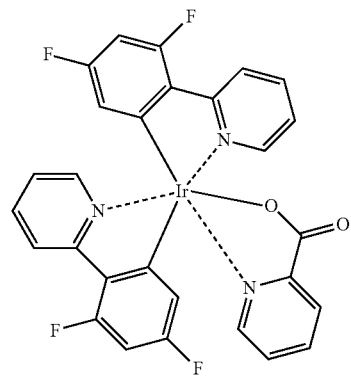

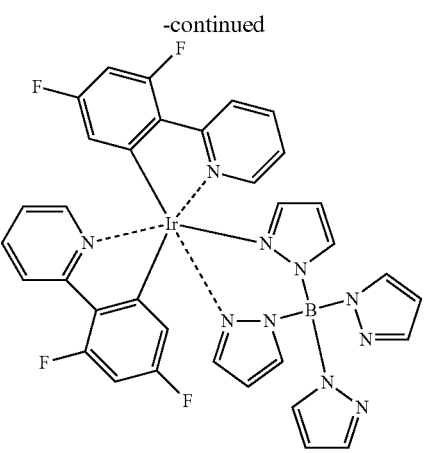

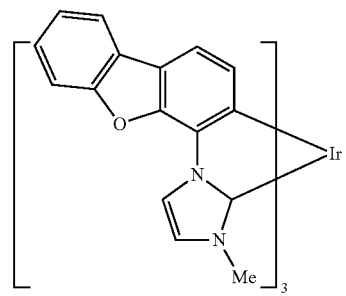

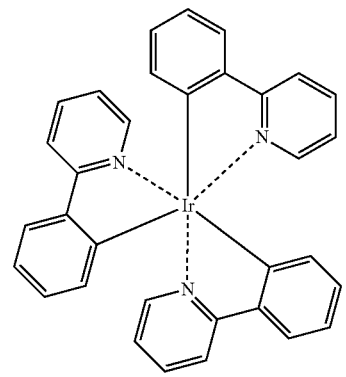

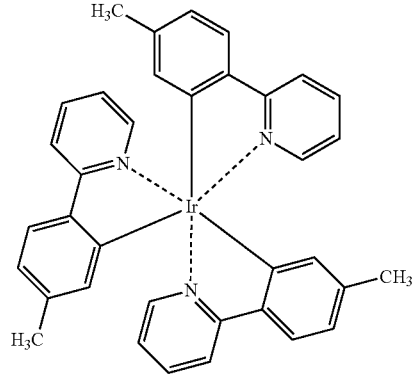

-continued
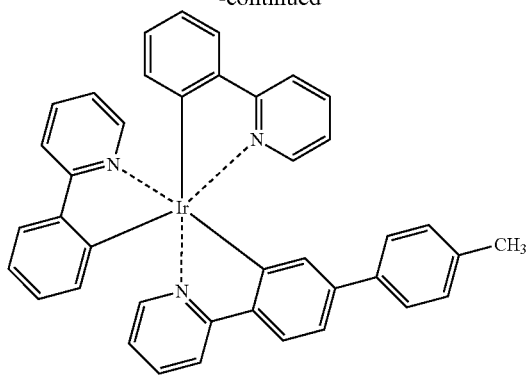
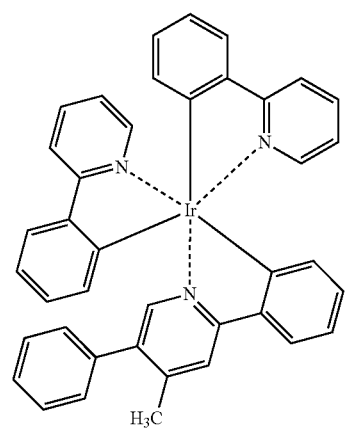
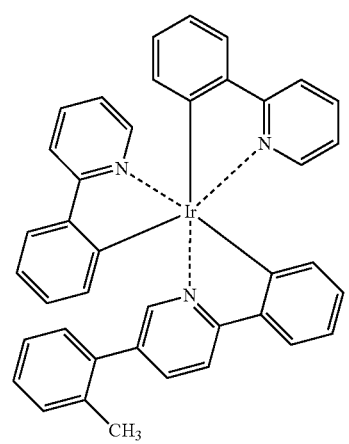
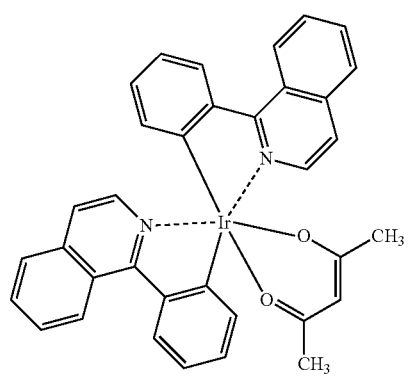
-continued
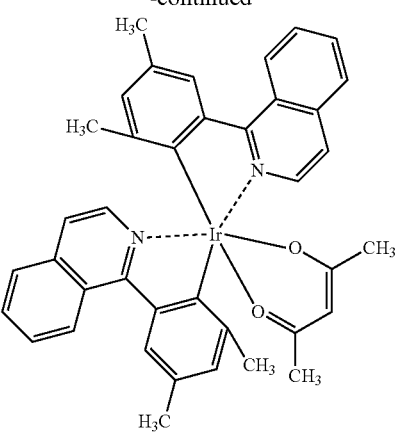
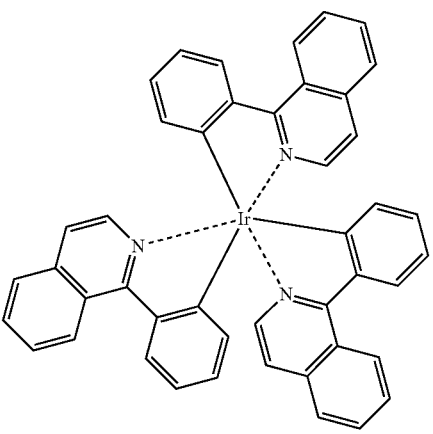
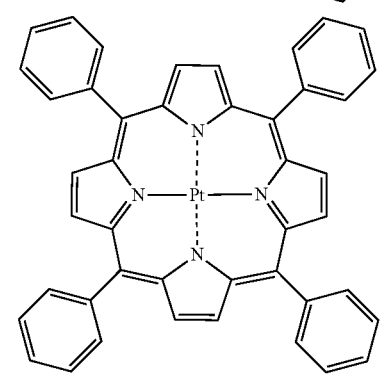
[Chemical Formula 12]
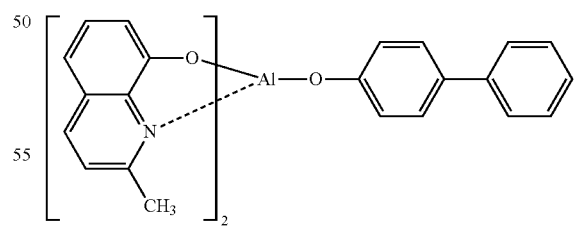
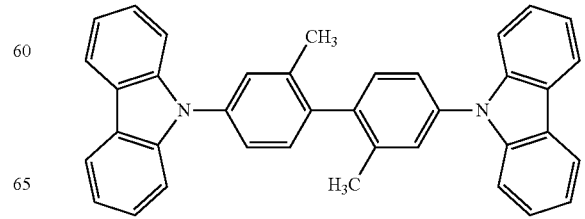

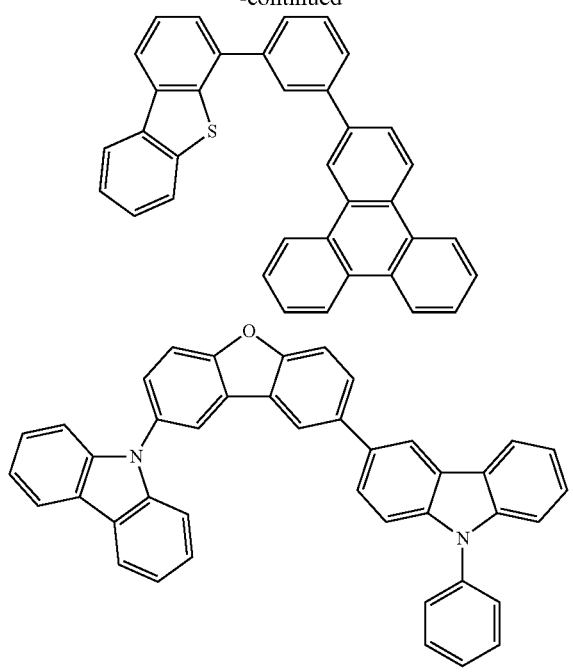
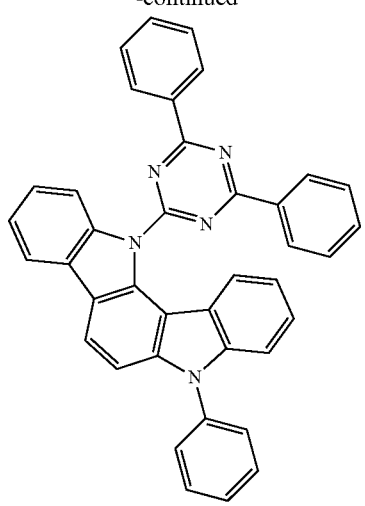
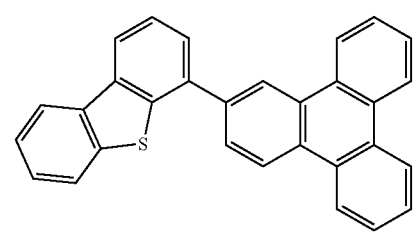
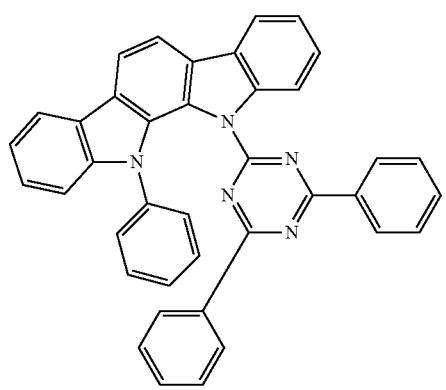
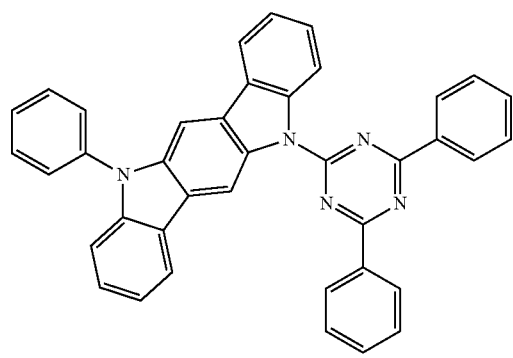
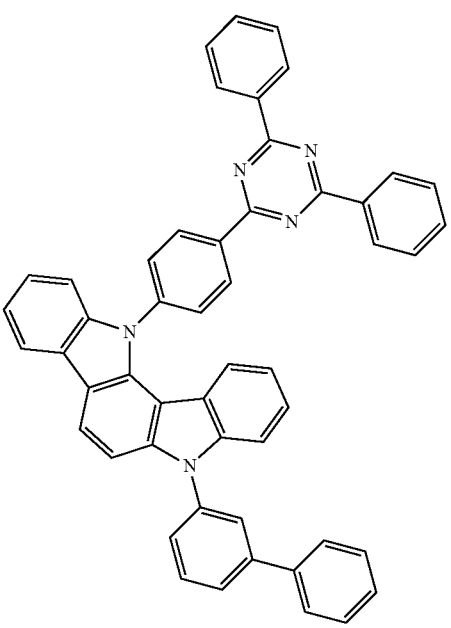

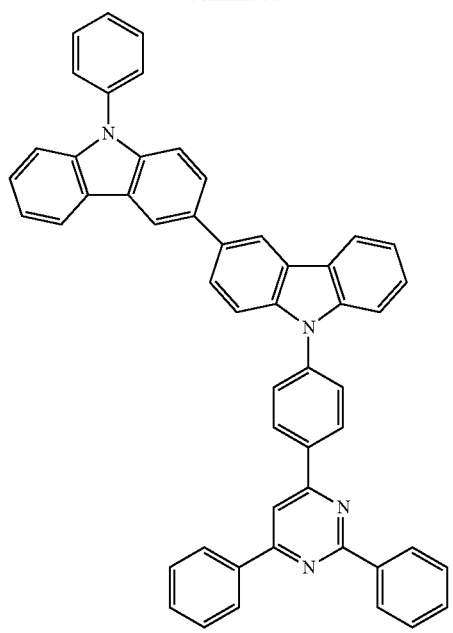
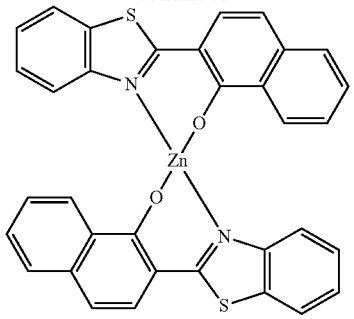
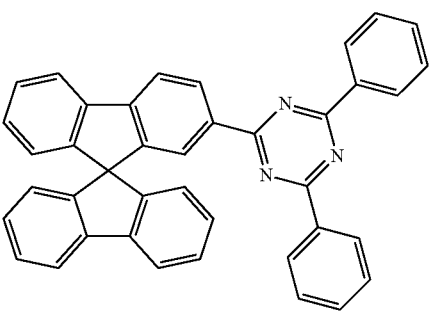
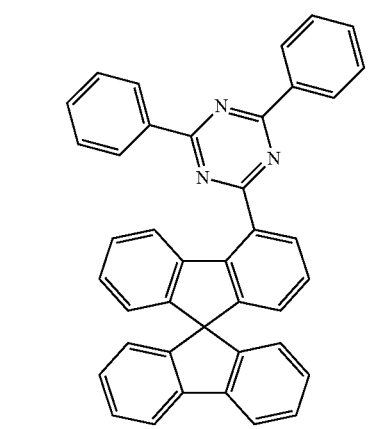
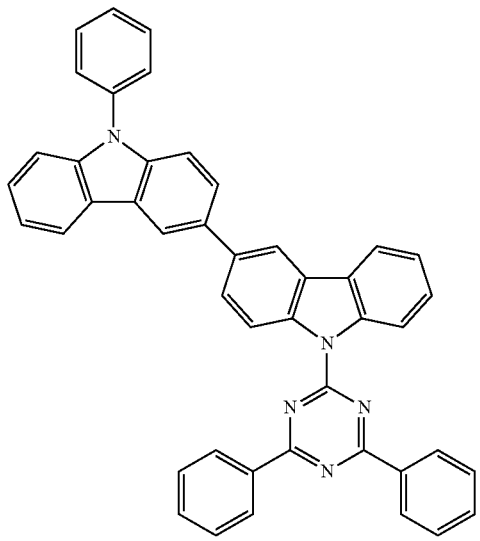

-continued

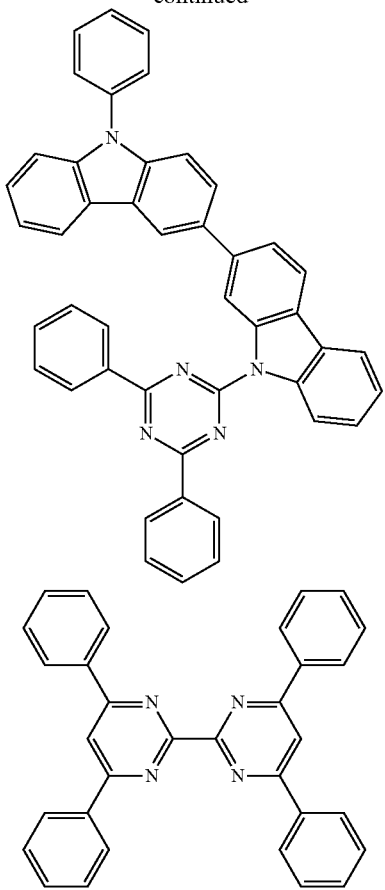

In the present invention, the electron transporting layer is a layer in which electrons are injected from the cathode and, further, which transports the electrons. It is desired that the electron transporting layer has a high electron injection efficiency, and efficiently transports injected electrons. For this reason, it is required that the electron transporting layer is constituted by a substance having great electron affinity and, moreover, great electron mobility and, further, excellent stability, and generating impurities that become a trap with difficulty at the time of production and at the time of use. In particular, when layers are laminated at a large thickness, since a low-molecular weight compound is crystallized etc., and the film quality is easily deteriorated, a compound having a molecular weight of 400 or more which retains stable film quality is preferable. However, when transportation balance between holes and electrons is considered, if the electron transporting layer mainly plays a role of being able to inhibiting holes from the anode from flowing to the cathode side without recombination, even when the layer is constituted by a material having not so high electron transporting ability, the effect of improving luminous efficiency becomes equivalent to that when the layer is constituted by a material having high electron transporting ability. Therefore, the electron transporting layer in the present invention also includes a hole inhibition layer which can efficiently inhibit the transfer of holes as the same meaning.

Examples of the electron transporting material to be used for the electron transporting layer include fused polycyclic aromatic derivatives, such as naphthalene and anthracene, styryl-based aromatic derivatives typified by 4,4'-bis(diphenylethenyl)biphenyl, quinone derivatives, such as anthraquinone and diphenoquinone, phosphorus oxide derivatives, and various types of metal complexes, such as quinolinol complexes, e.g., tris(8-quinolinolate)aluminum(III), benzoquinolinol complexes, hydroxyazole complexes, azomethine complexes, tropolone metal complexes, and flavonol metal complexes. It is preferred to use a compound that includes an device selected from carbon, hydrogen, nitrogen, oxygen, silicon, and phosphorus and has a heteroaryl ring structure containing an electron-accepting nitrogen because it can reduce a driving voltage and a highly efficient light emission can be obtained.

The electron-accepting nitrogen referred to herein denotes a nitrogen atom which forms a multiple bond between adjoining atoms. Since nitrogen atoms have high electronegativity, the multiple bond has an electron-accepting nature. For this reason, an aromatic heterocyclic ring containing electron-accepting nitrogen has high electron affinity. An electron transporting material having electron-accepting nitrogen makes easier acceptance of electrons from a cathode having higher electron affinity, and lower voltage driving becomes possible. In addition, since supply of electrons to an emissive layer is increased and a recombining probability is increased, luminous efficiency is increased.

Examples of the heteroaryl ring containing electron-accepting nitrogen include a pyridine ring, a pyrazine ring, a pyrimidine ring, a quinoline ring, a quinoxaline ring, a naphthylidine ring, a pyrimidopyrimidine ring, a benzoquinoline ring, a phenanthroline ring, an imidazole ring, an oxazole ring, an oxadiazole ring, a triazole ring, a thiazole ring, a thiadiazole ring, a benzoxazole ring, a benzothiazole ring, a benzimidazole ring, and a phenanthroimidazole ring.

Examples of preferred compounds having such a heteroaryl ring structure include benzimidazole derivatives, benzoxazole derivatives, benzthiazole derivatives, oxadiazole derivatives, thiadiazole derivatives, triazole derivatives, pyrazine derivatives, phenanthroline derivatives, quinoxaline derivatives, quinoline derivatives, benzoquinoline derivatives, oligopyridine derivatives such as bipyridine and terpyridine, quinoxaline derivatives and naphthylidine derivatives. Among them, imidazole derivatives such as tris(N-phenylbenzimidazol-2-yl)benzene; oxadiazole derivatives such as 1,3-bis[(4-tert-butylphenyl)1,3,4-oxadiazolyl]phenylene; triazole derivatives such as N-naphthyl-2,5-diphenyl-1,3,4-triazole; phenanthroline derivatives such as bathocuproine and 1,3-bis(1,10-phenanthrolin-9-yl)benzene; benzoquinoline derivatives such as 2,2'-bis(benzo[h]quinolin-2-yl)-9,9'-spirobifluorene; bipyridine derivatives such as 2,5-bis(6'-(2',2"-bipyridyl))-1,1-dimethyl-3,4-diphenylsilole; terpyridine derivatives such as 1,3-bis(4'-(2,2': 6'2"-terpyridinyl))benzene; and naphthylidine derivatives such as bis(1-naphthyl)-4-(1,8-naphthylidin-2-yl)phenylphosphine oxide are suitably used in view of an electron transporting ability. It is more preferable that such a derivative has a fused polycyclic aromatic skeleton because if so, then the glass transition temperature will increase and an effect of reducing the voltage of a light-emitting device is great due to increased electron mobility. Moreover, considering the improvement in durable life of an device, the easiness of synthesis, and easy availability of raw materials, it is particularly preferable that the fused polycyclic aromatic skeleton is an anthracene skeleton, a pyrene skeleton, or a phenanthroline skeleton. While the electron transporting material may be used alone, two or more kinds of the electron transporting materials may be used in combination, or one or more kinds of other electron transporting materials may be used in a combination with the electron transporting material.
Preferable electron transporting materials are not particularly limited, and specific examples thereof include the following.
[Chemical Formula 13]
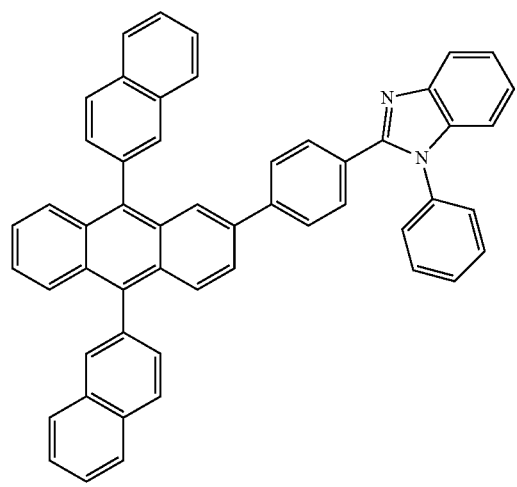
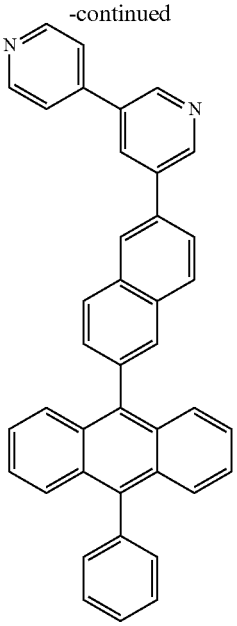
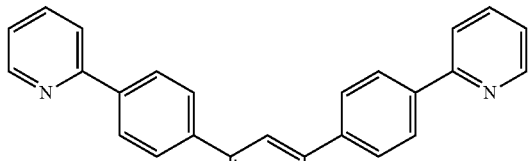
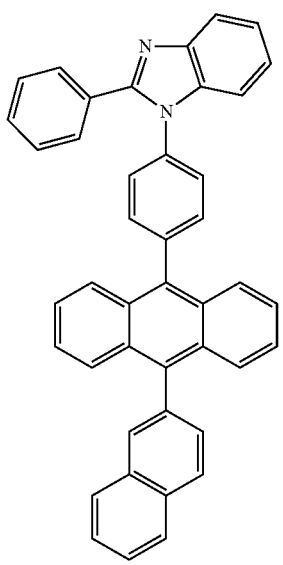
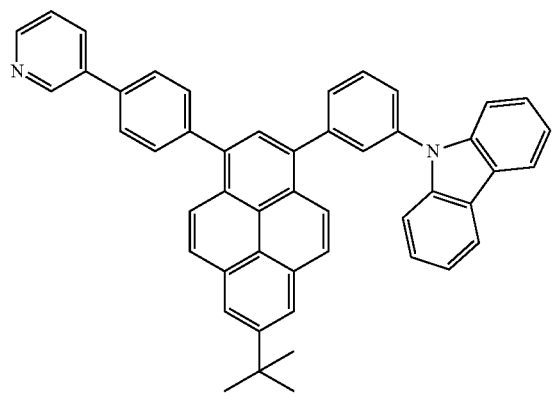

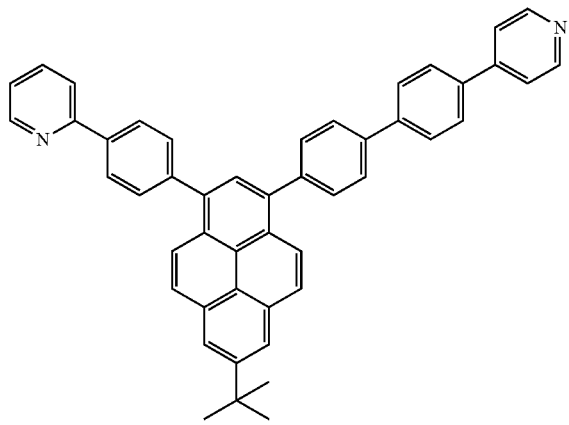
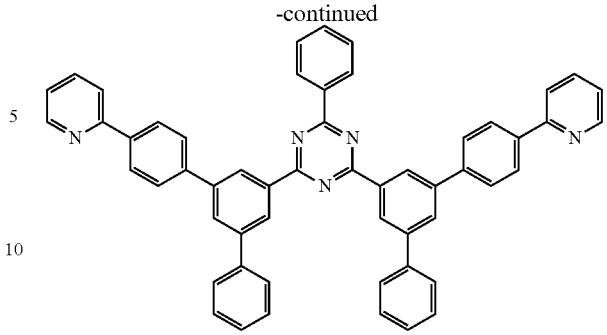
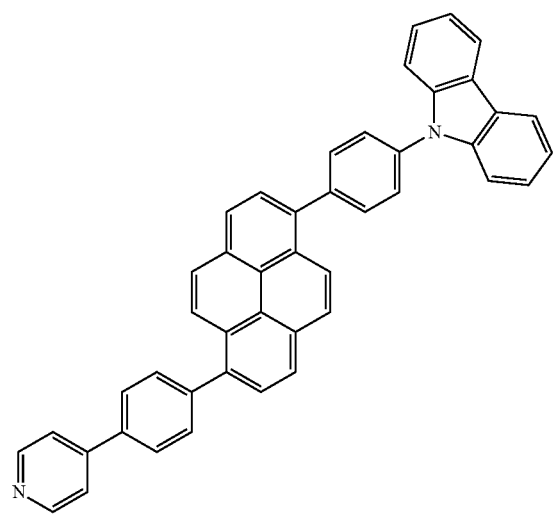
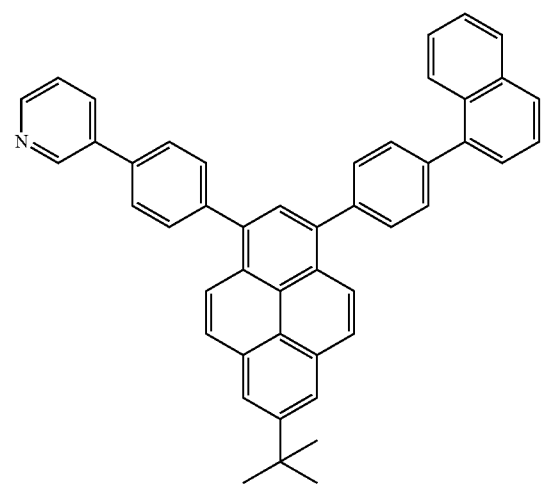
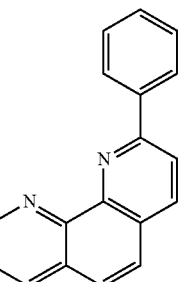

While the electron transporting material may be used alone, two or more kinds of the electron transporting materials may be used in combination, or one or more kinds of other electron transporting materials may be used in a combination with the electron transporting material. Moreover, a donor material may be contained. The donor material denotes a compound which makes easier electron injection into the electron transporting layer from the cathode or the electron injection layer and, further, improves the electric conductivity of the electron transporting layer, by improving an electron injection barrier.

Preferable examples of the donor material include an alkali metal, an inorganic salt containing an alkali metal, a complex of an alkali metal and an organic substance, an alkaline earth metal, an inorganic salt containing an alkaline earth metal, or a complex of an alkaline earth metal and an organic substance. Examples of the preferable kind of the alkali metal and the alkaline earth metal include alkali metals such as lithium, sodium, potassium, rubidium, and cesium, and alkaline earth metals such as magnesium, calcium, cerium, and barium which have a low work function and have a great effect of improving electron transporting ability.

In addition, since deposition in vacuum is easy, and handling is excellent, the donor compound is preferably in the state of an inorganic salt or a complex with an organic substance rather than a metal single substance. Moreover, from the viewpoints of improvement in easiness in handling in the atmospheric air, and easiness in control of the concentration to be added, the donor compound is more preferably in the state of a complex with an organic substance. Examples of the inorganic salt include oxides such as LiO and $Li_2O$, nitrides, fluorides such as LiF, NaF, and KF, and carbonates such as $Li_2CO_3$, $Na_2CO_3$, $K_2CO_3$, $Rb_2CO_3$, and $Cs_2CO_3$. Preferable examples of the alkali metal or alkaline earth metal include lithium and cesium from the viewpoint that a great low-voltage driving effect can be obtained. In addition, preferable examples of the organic substance in complexes with an organic substance include quinolinol, benzoquinolinol, pyridylphenol, flavonol, hydroxyimidazopyridine, hydroxybenzazole, and hydroxytriazole. Especially, a complex of an alkali metal and an organic substance is preferred from the viewpoint that the effect of reducing the voltage of a light-emitting device is greater, a complex of lithium and an organic substance is more preferred from the viewpoints of easiness in synthesis and thermal stability as well, and lithium quinolinol, which can be obtained relatively inexpensively, is particularly preferred.

The ionization potential of the electron transporting layer is not particularly limited, and is preferably 5.6 eV or more and 8.0 eV or less, and more preferably 5.6 eV or more and 7.0 eV or less.

Examples of a method of forming each of the aforementioned layers constituting the light-emitting device include, but are not particularly limited to, resistance heating deposition, electron beam deposition, sputtering, a molecular lamination method, and a coating method, but usually, resistance heating deposition or electron beam deposition is preferable from the viewpoint of device property.

The thickness of the organic layer depends on the resistance value of an emissive substance and, therefore, it cannot be limited, but it is preferably 1 to 1000 nm. The film thickness of each of the emissive layer, the electron transporting layer and the hole transporting layer is preferably 1 nm or more and 200 nm or less, more preferably 5 nm or more and 100 nm or less.

The light-emitting device of the present invention has a function of being able to convert electric energy into light. Herein, a direct current is mainly used as the electric energy, but a pulse current or an alternate current can also be used. A current value and a voltage value are not particularly limited, but when the power consumed and life of the device are considered, they should be selected so that the maximum luminance is obtained by energy as low as possible.

The light-emitting device of the present invention is used suitably as a display that displays in a matrix and/or segment system.

In the matrix system, pixels for display are arranged two-dimensionally such as lattice-like arrangement or mosaic-like arrangement, and the collection of pixels displays letters and images. The shape and size of the pixel are determined depending on utility. For example, for displaying images and letters on personal computers, monitors and televisions, a square pixel being 300 μm or less at each side is usually used, and, in the case of a large display such as a display panel, a pixel being millimeter order at each side is used. In the case of a monochromatic display, pixels having the same color may be arranged, and in the case of a color display, pixels having red, green and blue colors are arranged to perform display. In this case, typically, there are a delta type and a stripe type. A method of driving this matrix may be either a passive matrix driving method or an active matrix. The passive matrix driving has a simple structure, but when operation property is considered, the active matrix is more excellent in some cases, and it is necessary to use them properly depending on utility.

The segment system in the present invention is a system by which a pattern is formed so as to display predetermined information, and a region determined by arrangement of this pattern is made to emit light. Examples thereof include time and temperature displays in digital watches and thermometers, operating-state displays in audio equipment, IH cookers and so on, and panel displays of automobiles. The above-mentioned matrix display and segment display may exist together in the same panel.

The light-emitting device of the present invention can also be preferably used as backlight of various instruments. Backlight is used mainly for the purpose of improving the visibility of display apparatuses which do not emit light by themselves, and is used in liquid crystal display equipment, clocks, audio equipment, automobile panels, display panels, signs, etc. In particular, the light-emitting device of the present invention is preferably used in backlight for liquid crystal display apparatuses, inter alia, for personal computers which are studied to be thinned, and can provide backlight thinner and lighter than conventional products.

EXAMPLES

The present invention will be described by way of Examples, but the present invention is not limited thereto. In addition, the number of a compound in each of Examples described below indicates the number of the aforementioned compound.

The minimum excitation triplet energy T1 of each compound was measured in the following manner. A 10 μmol/l solution of each compound was prepared with 2-methyltetrahydrofuran as a solvent. Phosphorescence measurement was performed in a quartz cell at 77 K using Fluorescence Phosphorescence Spectrophotometer Fluoromax-4P (manufactured by HORIBA, Ltd.), a tangential line was drawn to a rise on the short wavelength side of the obtained phosphorescence spectrum, a wavelength at an intersection of the abscissa (light emitting end) was determined, and the wavelength was converted into an energy value.

Synthesis Example 1

Synthesis of Compound [2]

A mixed solution of 20.9 g of 3-bromocarbazole, 15.0 g of 9-phenylcarbazole-3-boronic acid, 366 mg of palladium acetate, 300 mg of tris(2-methylphenyl)phosphine, 105 ml of a 2M aqueous potassium carbonate solution and 260 ml of dimethoxyethane was refluxed for 6 hours under a nitrogen flow. The solution was cooled to room temperature, and then extracted with 500 ml of tetrahydrofuran. The organic layer was washed with 100 ml of a saturated saline solution twice, dried over magnesium sulfate, and then evaporated. The resultant concentrate was purified by o-xylene recrystallization and then vacuum-dried to obtain 13.5 g of 9-phenyl-9H,9'H-3,3'-bicarbazole.

Next, a mixed solution of 11.4 g of 9-phenyl-9H,9'H-3,3'-bicarbazole, 10.0 g of 3-bromotriphenylamine, 161 mg of bis(dibenzylideneacetone)palladium, 198 mg of di-t-butyl (2,2-diphenyl-1-methyl-1-cyclopropyl)phosphine, 3.8 g of sodium tert-butoxide and 140 ml of o-xylene was heated/stirred for 2 hours under reflux under a nitrogen flow. The solution was cooled to room temperature, and then extracted with 100 ml of toluene. The organic layer was washed with 80 ml of water three times, dried over magnesium sulfate, and then evaporated. The resultant concentrate was purified by silica gel column chromatography and evaporated to obtain a solid, and the solid was vacuum-dried to obtain 17.0 g of a white solid.

$^1$H-NMR analytical results of the resulting powder are as follows, and it was confirmed that the resulting white solid was a compound [2].

$^1$H-NMR (CDCl$_3$ (d=ppm)): 7.06 (t, 2H, J=7.3Hz), 7.15-7.35 (m, 13H), 7.39-7.54 (m, 8H), 7.60-7.64 (m, 4H), 7.76 (d, 2H, J=8.4Hz), 8.18-8.26 (m, 2H), 8.43 (dd, 2H, J=1.6Hz, 8.1Hz).

The compound [2] was used as a light-emitting device material after sublimation purification was performed at about 290° C. under a pressure of $1 \times 10^{-3}$ Pa using an oil diffusion pump. The HPLC purity (area % at a measurement wavelength of 254 nm) was 99.7% before sublimation purification, and 99.9% after sublimation purification. The minimum excitation triplet energy T1 of the compound [2] was 2.76 eV.

Synthesis Example 2

Synthesis of Compound [8]

A white solid was obtained by performing synthesis in the same manner as in Synthesis Example 1 except that 3-chloro-N,N-di-p-tolylaniline was used in place of 3-chloro-N,N-diphenylaniline.

$^1$H-NMR analytical results of the resulting powder are as follows, and it was confirmed that the resulting white solid was a compound [8].

$^1$H-NMR (CDCl$_3$ (d=ppm)): 2.31 (s, 6H), 7.06-7.22 (m, 10H), 7.28-7.67 (m, 15H), 7.74-7.78 (m, 2H), 8.18-8.26 (m, 2H), 8.41-8.45 (m, 2H).

The compound [8] was used as a light-emitting device material after sublimation purification was performed at about 320° C. under a pressure of 1×10$^{-3}$ Pa using an oil diffusion pump. The HPLC purity (area % at a measurement wavelength of 254 nm) was 99.6% before sublimation purification, and 99.9% after sublimation purification. The minimum excitation triplet energy T1 of the compound [8] was 2.76 eV.

Synthesis Example 3

Synthesis of Compound [31]

A white solid was obtained by performing synthesis in the same manner as in Synthesis Example 1 except that N-(3-chlorophenyl)-N-phenyl-[1,1'-biphenyl]-4-amine was used in place of 3-bromotriphenylamine.

$^1$H-NMR analytical results of the resulting powder are as follows, and it was confirmed that the resulting white solid was a compound [31].

$^1$H-NMR (CDCl$_3$ (d=ppm)): 7.06-7.79 (m, 33H), 8.19-8.25 (m, 2H), 8.41-8.44 (m, 2H).

The compound [31] was used as a light-emitting device material after sublimation purification was performed at about 350° C. under a pressure of 1×10$^{-3}$ Pa using an oil diffusion pump. The HPLC purity (area % at a measurement wavelength of 254 nm) was 99.5% before sublimation purification, and 99.9% after sublimation purification. The minimum excitation triplet energy T1 of the compound [31] was 2.60 eV.

Synthesis Example 4

Synthesis of Compound [32]

A white solid was obtained by performing synthesis in the same manner as in Synthesis Example 1 except that N-(3-chlorophenyl)-N-phenyl-[1,1'-biphenyl]-3-amine was used in place of 3-bromotriphenylamine.

$^1$H-NMR analytical results of the resulting powder are as follows, and it was confirmed that the resulting white solid was a compound [32].

$^1$H-NMR (CDCl$_3$ (d=ppm)): 7.06-7.76 (m, 33H), 8.17-8.26 (m, 2H), 8.39-8.42 (m, 2H).

The compound [32] was used as a light-emitting device material after sublimation purification was performed at about 350° C. under a pressure of 1×10$^{-3}$ Pa using an oil diffusion pump. The HPLC purity (area % at a measurement wavelength of 254 nm) was 99.7% before sublimation purification, and 99.9% after sublimation purification. The minimum excitation triplet energy T1 of the compound [32] was 2.60 eV.

Synthesis Example 5

Synthesis of Compound [33]

A mixed solution of 3.2 g of 3-chloroaniline, 58.9 g of bromobenzene-d, 5.3 g of sodium tert-butoxide, 431 mg of bis(dibenzylideneacetone)palladium, 196 mg of tri-tert-butylphosphonium tetrafluoroborate and 50 ml of toluene was heated/stirred at 50° C. for 2 hours under a nitrogen flow. The solution was extracted with 50 ml of toluene, and the organic layer was washed with 30 ml of water three times, dried over magnesium sulfate, and then evaporated. The resultant concentrate was purified by silica gel column chromatography and then vacuum-dried to obtain 4.5 g of an intermediate.

Next, a mixed solution of 2.3 g of 9-phenyl-9H,9'H-3,3'-bicarbazole, 2.0 g of the intermediate, 35 mg of bis(dibenzylideneacetone)palladium, 42 mg of di-t-butyl(2,2-diphenyl-1-methyl-1-cyclopropyl)phosphine, 0.77 g of sodium tert-butoxide and 29 ml of o-xylene was heated/stirred for 1 hour under reflux under a nitrogen flow. The solution was cooled to room temperature, and then extracted with 100 ml toluene. The organic layer was washed with 100 ml of water three times, dried over magnesium sulfate, and then evaporated. The resultant concentrate was purified by silica gel column chromatography and evaporated to obtain a solid, and the solid was vacuum-dried to obtain 2.5 g of a white solid.

$^1$H-NMR analytical results of the resulting powder are as follows, and it was confirmed that the resulting white solid was a compound [33].

$^1$H-NMR (CDCl$_3$ (d=ppm)): 7.16-7.77 (m, 19H), 8.18-8.26 (m, 2H), 8.41-8.44 (d, 2H, J=8.37).

The compound [33] was used as a light-emitting device material after sublimation purification was performed at about 330° C. under a pressure of 1×10$^{-3}$ Pa using an oil diffusion pump. The HPLC purity (area % at a measurement wavelength of 254 nm) was 99.7% before sublimation purification, and 99.9% after sublimation purification. The minimum excitation triplet energy T1 of the compound [33] was 2.76 eV.

Synthesis Example 6

Synthesis of Compound [35]

A white solid was obtained by performing synthesis in the same manner as in Synthesis Example 1 except that 4-bromotriphenylamine was used in place of 3-bromotriphenylamine.

$^1$H-NMR analytical results of the resulting powder are as follows, and it was confirmed that the resulting white solid was a compound [35].

$^1$H-NMR (CDCl$_3$ (d=ppm)): 7.09 (t, 2H, J=7.2Hz), 7.21-7.27 (m, 5H), 7.30-7.36 (m, 8H), 7.62-7.64 (m, 4H), 7.76-7.81 (dt, 2H, J=7.8Hz), 8.22-8.26 (m, 2H), 8.45 (t, 2H, J=1.6Hz).

The compound [35] was used as a light-emitting device material after sublimation purification was performed at about 290° C. under a pressure of 1×10$^{-3}$ Pausing an oil diffusion pump. The HPLC purity (area % at a measurement wavelength of 254 nm) was 99.8% before sublimation purification, and 99.9% after sublimation purification. The minimum excitation triplet energy T1 of the compound [35] was 2.76 eV.

Synthesis Example 7

Synthesis of Compound [40]

A mixed solution of 4.5 g of 4-hydroxycarbazole, 360 ml of dichloromethane and 3.0 g of diisopropylamine was cooled to 0° C. under a nitrogen flow, and 8.3 g of trifluoromethanesulfonic anhydride was added dropwise. The mixed solution was stirred at room temperature for 2 hours, 50 ml of water was then poured, and the mixture was extracted with 50 ml of dichloromethane. The organic layer was washed with 50 ml of water twice, dried over magnesium sulfate, and then evaporated. The concentrate was purified by silica gel column chromatography and then vacuum-dried to obtain 7.0 g of 9H-carbazole-4-yl-trifluoromethanesulfonate.

Next, a mixed solution of 3.2 g of 9H-carbazole-4-yl-trifluoromethanesulfonate, 3.3 g of 9-phenylcarbazole-3-boronic acid, 22.6 ml of a 1 M aqueous sodium carbonate solution, 51 ml of 1,2-dimethoxyethane and 223 mg of bis(triphenylphosphine)paladium (II) dichloride was refluxed for 4 hours under a nitrogen flow. The solution was cooled to room temperature, and then extracted with toluene. The organic layer was washed with water twice, dried over magnesium sulfate, and then evaporated. The resultant concentrate was purified by silica gel column chromatography and then vacuum-dried to obtain 3.4 g of 9-phenyl-9H,9'H-3,4'-bicarbazole.

Next, a mixed solution of 3.0 g of 9-phenyl-9H,9'H-3,4'-bicarbazole, 2.86 g of 4-bromotriphenylamine, 42 mg of bis(dibenzylideneacetone)palladium, 52 mg of di-t-butyl(2,2-diphenyl-1-methyl-1-cyclopropyl)phosphine, 988 mg of sodium tert-butoxide and 37 ml of o-xylene was heated/stirred for 2 hours under reflux under a nitrogen flow. The solution was cooled to room temperature, and then extracted with 100 ml toluene. The organic layer was washed with 80 ml of water three times, dried over magnesium sulfate, and then evaporated. The resultant concentrate was purified by silica gel column chromatography and evaporated to obtain a solid, and the solid was vacuum-dried to obtain 4.1 g of a white solid.

$^1$H-NMR analytical results of the resulting powder are as follows, and it was confirmed that the resulting white solid was a compound [40].

$^1$H-NMR (CDCl$_3$ (d=ppm)): 6.92-6.97 (m, 2H), 7.07-7.74 (m, 27H), 8.13-8.16 (d, 2H, J=7.83), 8.43-8.44 (d, 2H, J=13.5).

The compound [40] was used as a light-emitting device material after sublimation purification was performed at about 300° C. under a pressure of $1\times10^{-3}$ Pa using an oil diffusion pump. The HPLC purity (area % at a measurement wavelength of 254 nm) was 99.8% before sublimation purification, and 99.9% after sublimation purification. The minimum excitation triplet energy T1 of the compound [40] was 2.69 eV.

Synthesis Example 8

Synthesis of Compound [50]

A mixed solution of 3.2 g of 4-chloroaniline, 58.9 g of bromobenzene-d, 5.3 g of sodium tert-butoxide, 431 mg of bis(dibenzylideneacetone)palladium, 196 mg of tri-tert-butylphosphonium tetrafluoroborate and 50 ml of toluene was heated/stirred at 50° C. for 2 hours under a nitrogen flow. The solution was extracted with 50 ml of toluene, and the organic layer was washed with 30 ml of water three times, dried over magnesium sulfate, and then evaporated. The resultant concentrate was purified by silica gel column chromatography and then vacuum-dried to obtain 4.5 g of an intermediate.

Next, a mixed solution of 2.3 g of 9-phenyl-9H,9'H-3,3'-bicarbazole, 2.0 g of the intermediate, 35 mg of bis(dibenzylideneacetone)palladium, 42 mg of di-t-butyl(2,2-diphenyl-1-methyl-1-cyclopropyl)phosphine, 0.77 g of sodium tert-butoxide and 29 ml of o-xylene was heated/stirred for 1 hour under reflux under a nitrogen flow. The solution was cooled to room temperature, and then extracted with 100 ml toluene. The organic layer was washed with 100 ml of water three times, dried over magnesium sulfate, and then evaporated. The resultant concentrate was purified by silica gel column chromatography and evaporated to obtain a solid, and the solid was vacuum-dried to obtain 2.5 g of a white solid.

$^1$H-NMR analytical results of the resulting powder are as follows, and it was confirmed that the resulting white solid was a compound [50].

$^1$H-NMR (CDCl$_3$ (d=ppm)): 7.29-7.79 (m, 19H), 8.23-8.26 (m, 2H), 8.45 (s, 2H).

The compound [50] was used as a light-emitting device material after sublimation purification was performed at about 330° C. under a pressure of $1\times10^{-3}$ Pausing an oil diffusion pump. The HPLC purity (area % at a measurement wavelength of 254 nm) was 99.7% before sublimation purification, and 99.9% after sublimation purification. The minimum excitation triplet energy T1 of the compound [50] was 2.76 eV.

Synthesis Example 9

Synthesis of Compound [53]

A white solid was obtained by performing synthesis in the same manner as in Synthesis Example 1 except that N-(4-chlorophenyl)-N-phenyl-[1,1'-biphenyl]-4-amine was used in place of 3-bromotriphenylamine.

$^1$H-NMR analytical results of the resulting powder are as follows, and it was confirmed that the resulting white solid was a compound [53].

$^1$H-NMR (CDCl$_3$ (d=ppm)): 7.12-7.62 (m, 31H), 7.77-7.78 (m, 2H), 8.23-8.26 (d, 2H, J=7.29), 8.46 (s, 2H).

The compound [53] was used as a light-emitting device material after sublimation purification was performed at about 330° C. under a pressure of $1\times10^{-3}$ Pa using an oil diffusion pump. The HPLC purity (area % at a measurement wavelength of 254 nm) was 99.5% before sublimation purification, and 99.9% after sublimation purification. The minimum excitation triplet energy T1 of the compound [53] was 2.61 eV.

Example 1

A glass substrate with an ITO transparent electroconductive film deposited thereon in a thickness of 50 nm (manufactured by GEOMATEC Co., Ltd., 11Ω/□, sputtered product) was cut into 38×46 mm, and etched. The resulting substrate was ultrasonically washed with "SEMICOCLEAN 56" (trade name, manufactured by Furuuchi Chemical Corporation) for 15 minutes, and then washed with ultrapure water. This substrate was treated with UV-ozone for 1 hour immediately before preparation of an device, and placed in a vacuum deposition apparatus, and the air was evacuated until the degree of vacuum in the apparatus was 5×10⁻⁴ Pa or lower. By a resistance heating method, a compound HI-1 was deposited as a hole injection layer in a thickness of 10 nm. Next, a compound HT-4 was deposited as a first hole transporting layer in a thickness of 80 nm. Next, a compound [2] was deposited as a second hole transporting layer in a thickness of 10 nm. Then, a compound H-1 and a compound D-1 were used as a host material and as a dopant material, respectively, and were deposited as an emissive layer in a thickness of 30 nm so that the doping concentration of the dopant material was 10% by weight. Next, a layer formed by mixing a compound E-1 and a donor material (Liq: lithium quinolinol) at a deposition speed ratio of 1:1 (=0.05 nm/s: 0.05 nm/s) was laminated as an electron transporting layer in a thickness of 35 nm.

Next, lithium quinolinol was deposited in a thickness of 1 nm, and co-deposited film of magnesium and silver was deposited in a thickness of 100 nm at a deposition speed ratio of magnesium:silver=10:1 (=0.5 nm/s:0.05 nm/s) to form a cathode, so that a 5×5 mm square device was prepared. The film thickness referred to herein was an indicated value on a crystal oscillation film thickness monitor. When this light-emitting device was direct-current driven at 10 mA/cm², high-efficiency green light emission with a luminous efficiency of 52.0 lm/W was obtained. When this light-emitting device was continuously driven at a direct current of 10 mA/cm², the luminance decreased by half after 3600 hours. Compounds HI-1, HT-4, H-1, D-1, and E-1 are the compounds shown below.

[Chemical Formula 14]

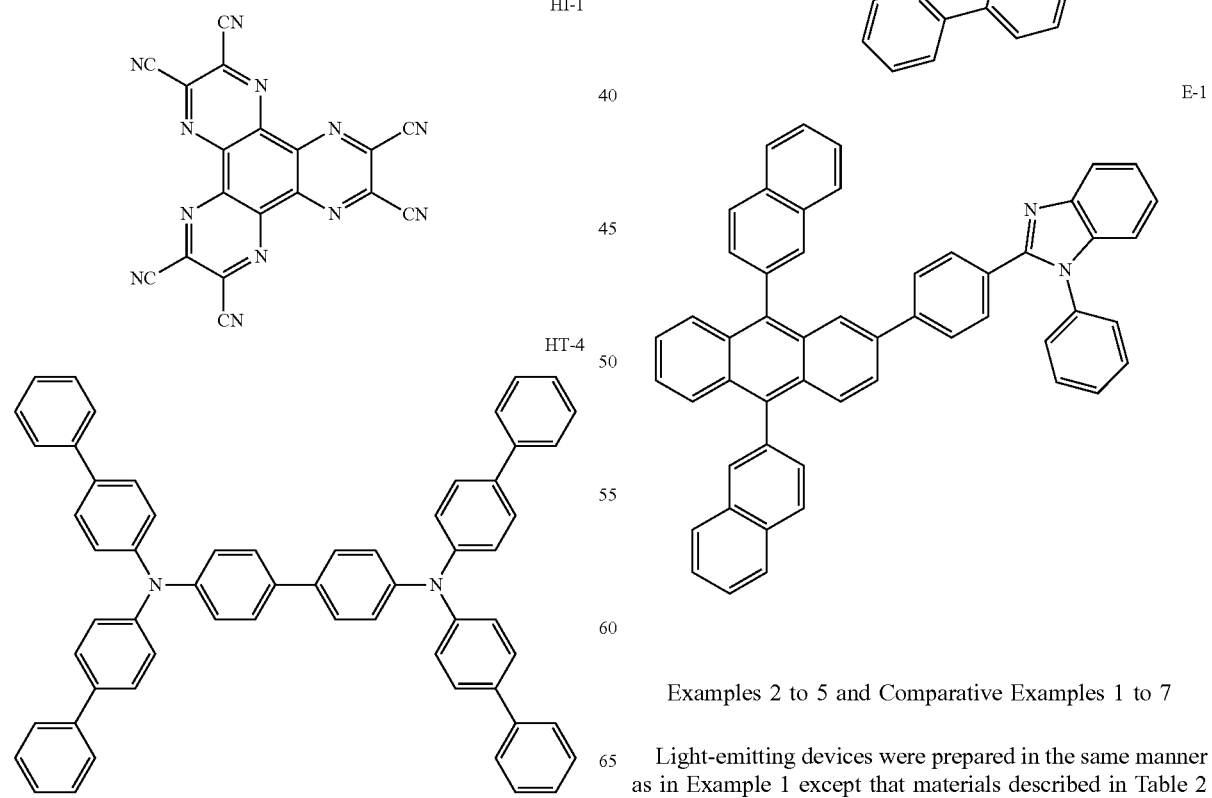

Examples 2 to 5 and Comparative Examples 1 to 7

Light-emitting devices were prepared in the same manner as in Example 1 except that materials described in Table 2 were used as a second hole transporting layer. The results are shown in Table 2. HT-1 to HT-7 are compounds shown below, and the minimum excitation triplet energy T1 thereof is as shown in Table 1.
[Chemical Formula 15]
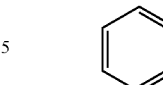
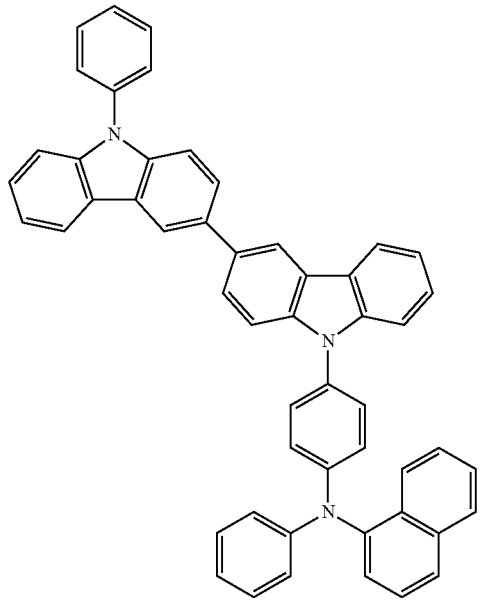
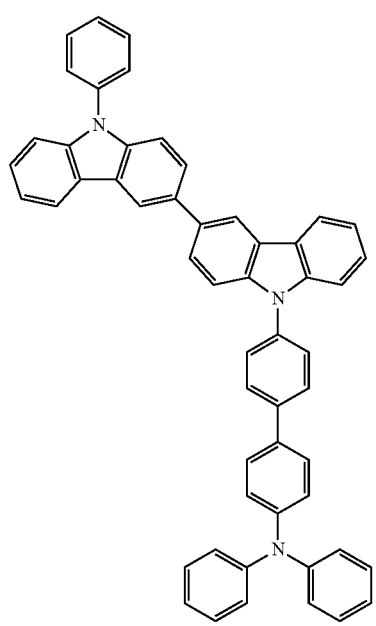
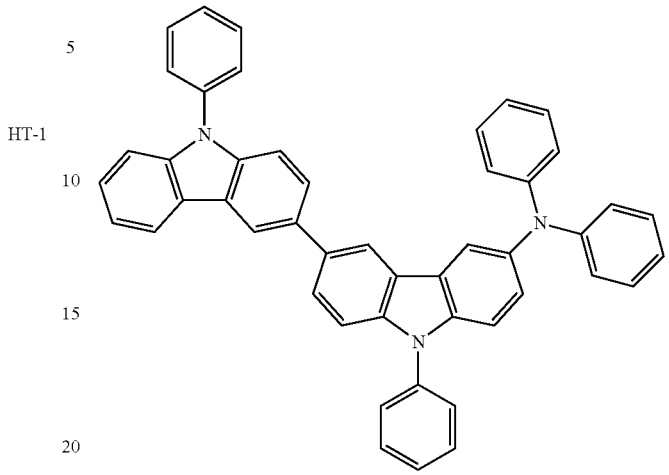
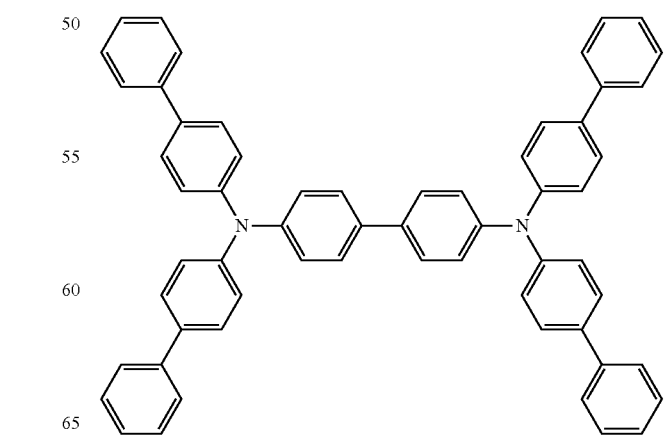

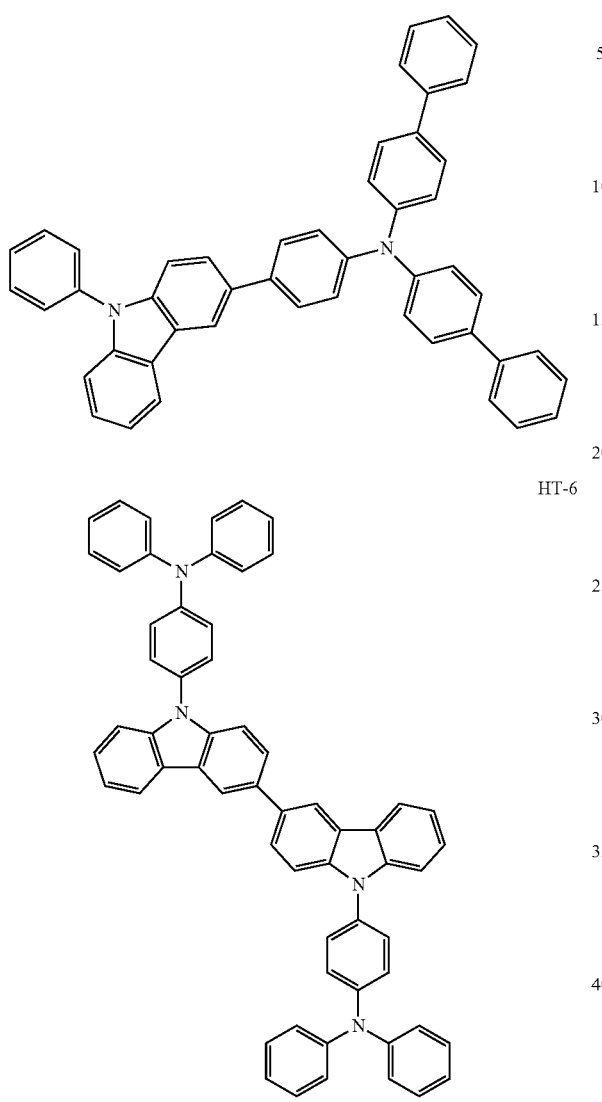

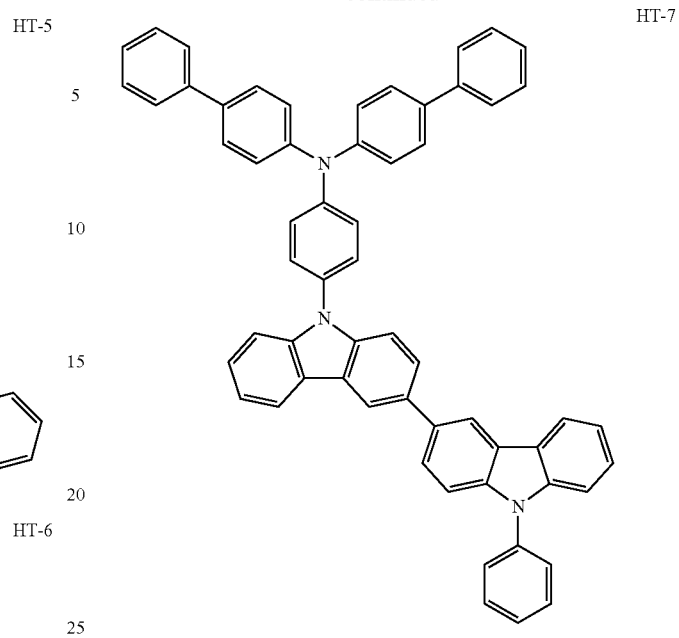

TABLE 1

| Compound | Triplet level (eV) |
| --- | --- |
| Compound [2] | 2.76 |
| Compound [8] | 2.76 |
| Compound [31] | 2.6 |
| Compound [32] | 2.6 |
| Compound [33] | 2.76 |
| Compound [35] | 2.76 |
| Compound [40] | 2.69 |
| Compound [50] | 2.76 |
| Compound [53] | 2.61 |
| HT-1 | 2.41 |
| HT-2 | 2.54 |
| HT-3 | 2.57 |
| HT-4 | 2.43 |
| HT-5 | 2.56 |
| HT-6 | 2.76 |
| HT-7 | 2.57 |

TABLE 2

| | Hole injection layer | First hole transporting layer | Second hole transporting layer | Host material | Dopant material | Electron transporting layer | Emitted color | Luminous efficiency (lm/W) | Luminance half-value period (h) |
| --- | --- | --- | --- | --- | --- | --- | --- | --- | --- |
| Example 1 | HI-1 | HT-4 | Compound [2] | H-1 | D-1 | E-1/Liq (dope) | Green | 52.0 | 3600 |
| Example 2 | HI-1 | HT-4 | Compound [8] | H-1 | D-1 | E-1/Liq (dope) | Green | 54.0 | 3700 |
| Example 3 | HI-1 | HT-4 | Compound [31] | H-1 | D-1 | E-1/Liq (dope) | Green | 55.0 | 4000 |
| Example 4 | HI-1 | HT-4 | Compound [32] | H-1 | D-1 | E-1/Liq (dope) | Green | 54.0 | 3900 |
| Example 5 | HI-1 | HT-4 | Compound [33] | H-1 | D-1 | E-1/Liq (dope) | Green | 52.0 | 3600 |
| Comparative Example 1 | HI-1 | HT-4 | HT-1 | H-1 | D-1 | E-1/Liq (dope) | Green | 29.0 | 1400 |
| Comparative Example 2 | HI-1 | HT-4 | HT-2 | H-1 | D-1 | E-1/Liq (dope) | Green | 29.0 | 1750 |
| Comparative Example 3 | HI-1 | HT-4 | HT-3 | H-1 | D-1 | E-1/Liq (dope) | Green | 26.0 | 1100 |
| Comparative Example 4 | HI-1 | HT-4 | HT-4 | H-1 | D-1 | E-1/Liq (dope) | Green | 27.0 | 1600 |
| Comparative Example 5 | HI-1 | HT-4 | HT-5 | H-1 | D-1 | E-1/Liq (dope) | Green | 28.0 | 1700 |
| Comparative Example 6 | HI-1 | HT-4 | HT-6 | H-1 | D-1 | E-1/Liq (dope) | Green | 31.0 | 1200 |

TABLE 2-continued

| | Hole injection layer | First hole transporting layer | Second hole transporting layer | Host material | Dopant material | Electron transporting layer | Emitted color | Luminous efficiency (lm/W) | Luminance half-value period (h) |
|---|---|---|---|---|---|---|---|---|---|
| Comparative Example 7 | HI-1 | HT-4 | HT-7 | H-1 | D-1 | E-1/Liq (dope) | Green | 31.0 | 1800 |

Examples 6 to 8

Light-emitting devices were prepared in the same manner as in Example 1 except that materials described in Table 2 were used as the second transporting layer, and a mixed host of a compound H-2 and a compound H-3 was used in place of the compound H-1 as a host material. A co-deposited film of the compound H-2 and the compound H-3 was deposited at a deposition speed ratio of 1:1, and further a dopant was deposited in a doping concentration of 10% by weight. The results are shown in Table 3. H-2 and H-3 are compounds shown below.

[Chemical Formula 16]

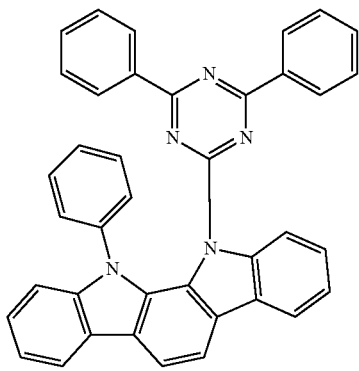
H-2

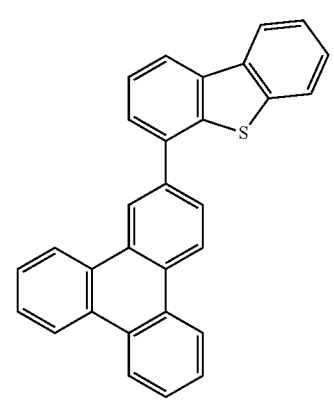
H-3

Examples 9 to 11

Light-emitting devices were prepared in the same manner as in Example 1 except that materials described in Table 2 were used as the second hole transporting layer, and the electron transporting layer was laminated in a two-layer deposited configuration by depositing a compound E-2 as a first electron transporting layer in a thickness of 10 nm and depositing a co-deposited film of a compound E-3 and a donor metal (Li: lithium) as a second electron transporting layer in a thickness of 25 nm at a deposition speed ratio of 100:1 (=0.2 nm/s 0.002 nm/s). The results are shown in Table 3. E-2 and E-3 are compounds shown below.

[Chemical Formula 17]

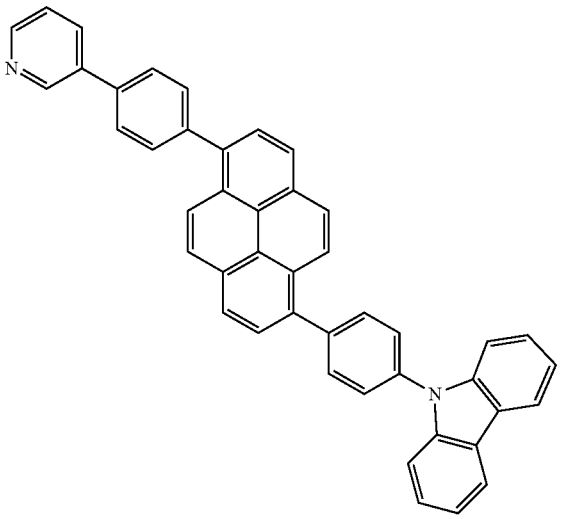
E-2

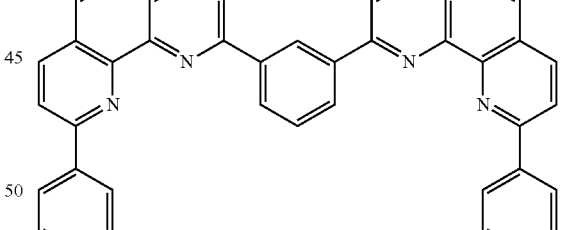
E-3

Examples 12 to 14

Light-emitting devices were prepared in the same manner as in Example 1 except that materials described in Table 2 were used as the second hole transporting layer, a compound [2] and a compound HI-2 were used in place of the compound HI-1, and were deposited in a thickness of 10 nm so that the doping concentration of the compound HI-2 was 5% by weight with respect to the compound [2] in the hole injection layer. The results are shown in Table 3. HI-2 is the compound shown below.

[Chemical Formula 18]

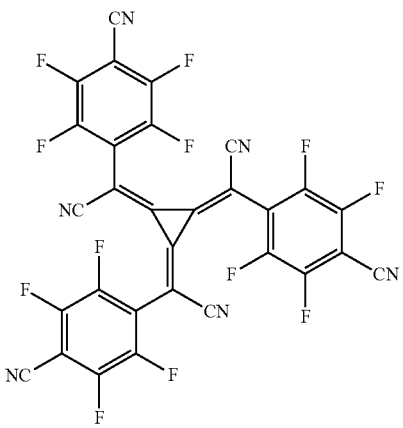

HI-2

Example 15

A glass substrate with an ITO transparent electroconductive film deposited thereon in a thickness of 50 nm (manufactured by GEOMATEC Co., Ltd., 11Ω/□, sputtered product) was cut into 38×46 mm, and etched. The resulting substrate was ultrasonically washed with "SEMICOCLEAN 56" (trade name, manufactured by Furuuchi Chemical Corporation) for 15 minutes, and then washed with ultrapure water. This substrate was treated with UV-ozone for 1 hour immediately before preparation of an device, and placed in a vacuum deposition apparatus, and the air was evacuated until the degree of vacuum in the apparatus was $5 \times 10^{-4}$ Pa or lower. By a resistance heating method, a compound HI-1 was deposited as a hole injection layer in a thickness of 10 nm. Next, a compound HT-4 was deposited as a first hole transporting layer in a thickness of 80 nm. Next, a compound [2] was deposited as a second hole transporting layer in a thickness of 10 nm. Then, a compound H-2 and a compound D-2 were used as a host material and as a dopant material, respectively, and were deposited as an emissive layer in a thickness of 30 nm so that the doping concentration of the dopant material was 10% by weight. Next, a compound E-3 was laminated as an electron transporting layer in a thickness of 35 nm.

Next, lithium quinolinol was deposited in a thickness of 1 nm, and co-deposited film of magnesium and silver was deposited in a thickness of 100 nm at a deposition speed ratio of magnesium:silver=10:1 (=0.5 nm/s:0.05 nm/s) to form a cathode, so that a 5×5 mm square device was prepared. The film thickness referred to herein was an indicated value on a crystal oscillation film thickness monitor. When this light-emitting device was direct-current driven at 10 mA/cm², high-efficiency green light emission with a luminous efficiency of 43.0 lm/W was obtained. When this light-emitting device was continuously driven at a direct current of 10 mA/cm², the luminance decreased by half after 3000 hours. D-2 is the compound shown below.

[Chemical Formula 19]

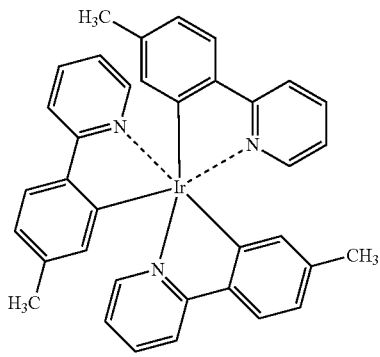

D-2

Example 16

Light-emitting devices were each prepared in the same manner as in Example 15 except that a mixed host of a compound H-2 and a compound H-3 was used in place of the compound H-2 as a host material. A co-deposited film of the compound H-2 and the compound H-3 was deposited at a deposition speed ratio of 1:1, and further a dopant was deposited in a doping concentration of 10% by weight. The results are shown in Table 3.

Example 17

A light-emitting device was prepared in the same manner as in Example 15 except that as the electron transporting layer, a layer was laminated by depositing a mixture of a compound E-1 and a donor material (Liq: lithium quinolinol) in place of the compound E-3 at a deposition speed ratio of 1:1 (=0.05 nm/s:0.05 nm/s). The results are shown in Table 3.

TABLE 3

| | Hole injection layer | First hole transporting layer | Second hole transporting layer | Host material | Dopant material | Electron transporting layer | Emitted color | Luminous efficiency (lm/W) | Luminance half-value period (h) |
|---|---|---|---|---|---|---|---|---|---|
| Example 6 | HI-1 | HT-4 | Compound [2] | H-2/H-3 | D-1 | E-1/Liq (dope) | Green | 53.0 | 4400 |
| Example 7 | HI-1 | HT-4 | Compound [8] | H-2/H-3 | D-1 | E-1/Liq (dope) | Green | 54.0 | 4500 |
| Example 8 | HI-1 | HT-4 | Compound [31] | H-2/H-3 | D-1 | E-1/Liq (dope) | Green | 58.0 | 5100 |
| Example 9 | HI-1 | HT-4 | Compound [2] | H-1 | D-1 | First layer E-2 Second layer E-3/Li (dope) | Green | 54.0 | 4000 |
| Example 10 | HI-1 | HT-4 | Compound [31] | H-1 | D-1 | First layer E-2 Second layer E-3/Li (dope) | Green | 59.0 | 5000 |
| Example 11 | HI-1 | HT-4 | Compound [32] | H-1 | D-1 | First layer E-2 Second layer E-3/Li (dope) | Green | 58.0 | 4700 |
| Example 12 | Compound [2]/HI-2 | HT-4 | Compound [2] | H-1 | D-1 | E-1/Liq (dope) | Green | 55.0 | 4200 |
| Example 13 | Compound [2]/HI-2 | HT-4 | Compound [31] | H-1 | D-1 | E-1/Liq (dope) | Green | 59.0 | 5200 |

TABLE 3-continued

| | Hole injection layer | First hole transporting layer | Second hole transporting layer | Host material | Dopant material | Electron transporting layer | Emitted color | Luminous efficiency (lm/W) | Luminance half-value period (h) |
|---|---|---|---|---|---|---|---|---|---|
| Example 14 | Compound [2]/HI-2 | HT-4 | Compound [32] | H-1 | D-1 | E-1/Liq (dope) | Green | 58.0 | 4800 |
| Example 15 | HI-1 | HT-4 | Compound [2] | H-2 | D-2 | E-3 | Green | 43.0 | 3000 |
| Example 16 | HI-1 | HT-4 | Compound [2] | H-2/H-3 | D-2 | E-3 | Green | 40.0 | 4200 |
| Example 17 | HI-1 | HT-4 | Compound [2] | H-2 | D-2 | E-1/Liq (dope) | Green | 44.0 | 5000 |

Example 18

A glass substrate with an ITO transparent electroconductive film deposited thereon in a thickness of 50 nm (manufactured by GEOMATEC Co., Ltd., 11Ω/□, sputtered product) was cut into 38×46 mm, and etched. The resulting substrate was ultrasonically washed with "SEMICOCLEAN 56" (trade name, manufactured by Furuuchi Chemical Corporation) for 15 minutes, and then washed with ultrapure water. This substrate was treated with UV-ozone for 1 hour immediately before preparation of an device, and placed in a vacuum deposition apparatus, and the air was evacuated until the degree of vacuum in the apparatus was $5 \times 10^{-4}$ Pa or lower. By a resistance heating method, a compound HI-1 was deposited as a hole injection layer in a thickness of 10 nm. Next, a compound HT-4 was deposited as a first hole transporting layer in a thickness of 50 nm. Next, a compound [2] was deposited as a second hole transporting layer in a thickness of 40 nm. Then, a compound H-4 and a compound D-3 were used as a host material and as a dopant material, respectively, and were deposited as an emissive layer in a thickness of 30 nm so that the doping concentration of the dopant material was 5% by weight. Next, a compound E-3 was laminated as an electron transporting layer in a thickness of 35 nm.

Next, lithium fluoride was deposited in a thickness of 0.5 nm, and aluminum was deposited in a thickness of 1000 nm to forma cathode, so that a 5×5 mm square device was prepared. The film thickness referred to herein was an indicated value on a crystal oscillation film thickness monitor. When this light-emitting device was direct-current driven at 10 mA/cm$^2$, high-efficiency red light emission with a luminous efficiency of 13.0 lm/W was obtained. When this light-emitting device was continuously driven at a direct current of 10 mA/cm$^2$, the luminance decreased by half after 3000 hours. Compounds H-4 and D-3 are compounds shown below.

[Chemical Formula 20]

H-4

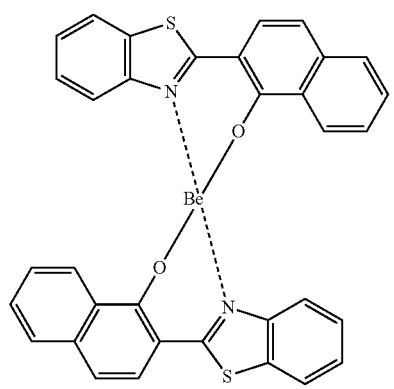

-continued

D-3

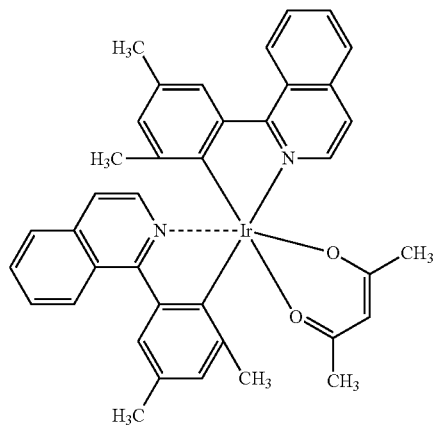

Examples 19 to 20

In the same manner as in Example 18 except that materials described in Table 4 were used as a second hole transporting layer, light-emitting devices were prepared and evaluated. The results are shown in Table 4.

Comparative Examples 8 to 12

In the same manner as in Example 18 except that compounds described in Table 4 were used as a second hole transporting layer, light-emitting devices were prepared and evaluated. The results are shown in Table 4.

Examples 21 to 22

Light-emitting devices were prepared in the same manner as in Example 18 except that materials described in Table 4 were used as the second hole transporting layer, and the electron transporting layer was laminated in a two-layer deposited configuration by depositing a compound E-4 as a first electron transporting layer in a thickness of 25 nm and depositing a compound E-3 as a second electron transporting layer in a thickness of 10 nm. The results are shown in Table 4.

[Chemical Formula 21]

E-4

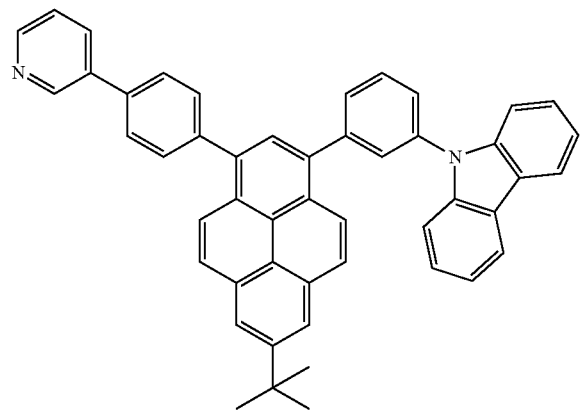

Then, a compound H-5 and a compound D-4 were used as a host material and as a dopant material, respectively, and were deposited as an emissive layer in a thickness of 40 nm so that the doping concentration of the dopant material was 5% by weight. Next, a layer formed by mixing a compound E-1 and a donor material (Liq: lithium quinolinol) at a deposition speed ratio of 1:1 (=0.05 nm/s:0.05 nm/s) was laminated as an electron transporting layer in a thickness of 35 nm.

Next, lithium fluoride was deposited in a thickness of 0.5 nm and aluminum was deposited in a thickness of 60 nm to form a cathode, so that a 5×5 mm square device was prepared. The film thickness referred to herein was an indicated value on a crystal oscillation film thickness monitor. When this light-emitting device was direct-current

TABLE 4

| | Hole injection layer | First hole transporting layer | Second hole transporting layer | Host material | Dopant material | Electron transporting layer | Emitted color | Luminous efficiency (lm/W) | Luminance half-value period (h) |
|---|---|---|---|---|---|---|---|---|---|
| Example 18 | HI-1 | HT-4 | Compound [2] | H-4 | D-3 | E-3 | Red | 13.0 | 3000 |
| Example 19 | HI-1 | HT-4 | Compound [8] | H-4 | D-3 | E-3 | Red | 15.0 | 3300 |
| Example 20 | HI-1 | HT-4 | Compound [31] | H-4 | D-3 | E-3 | Red | 19.0 | 3500 |
| Comparative Example 8 | HI-1 | HT-4 | HI-1 | H-4 | D-3 | E-3 | Red | 7.3 | 1300 |
| Comparative Example 9 | HI-1 | HT-4 | HI-2 | H-4 | D-3 | E-3 | Red | 8.8 | 1000 |
| Comparative Example 10 | HI-1 | HT-4 | HI-3 | H-4 | D-3 | E-3 | Red | 6.6 | 900 |
| Comparative Example 11 | HI-1 | HT-4 | HI-4 | H-4 | D-3 | E-3 | Red | 9.0 | 1300 |
| Comparative Example 12 | HI-1 | HT-4 | HI-6 | H-4 | D-3 | E-3 | Red | 12.0 | 1000 |
| Example 21 | HI-1 | HT-4 | Compound [2] | H-4 | D-3 | First layer E-4 Second layer E-3 | Red | 12.5 | 3600 |
| Example 22 | HI-1 | HT-4 | Compound [31] | H-4 | D-3 | First layer E-4 Second layer E-3 | Red | 20.0 | 4000 |

Example 23

A glass substrate with an ITO transparent electroconductive film deposited thereon in a thickness of 50 nm (manufactured by GEOMATEC Co., Ltd., 11Ω/□, sputtered product) was cut into 38×46 mm, and etched. The resulting substrate was ultrasonically washed with "SEMICOCLEAN 56" (trade name, manufactured by Furuuchi Chemical Corporation) for 15 minutes, and then washed with ultrapure water. This substrate was treated with UV-ozone for 1 hour immediately before preparation of an device, and placed in a vacuum deposition apparatus, and the air was evacuated until the degree of vacuum in the apparatus was $5\times10^{-4}$ Pa or lower. By a resistance heating method, HI-1 was deposited as a hole injection layer in a thickness of 10 nm. Next, HT-4 was deposited as a first hole transporting layer in a thickness of 110 nm. Next, a compound [2] was deposited as a second hole transporting layer in a thickness of 10 nm.

driven at 10 mA/cm², blue light emission with a luminous efficiency of 4.8 lm/W was obtained. When this light-emitting device was continuously driven at a direct current of 10 mA/cm², the luminance decreased by half after 1800 hours. Compounds H-5 and D-4 are compounds shown below.

[Chemical Formula 22]

H-5

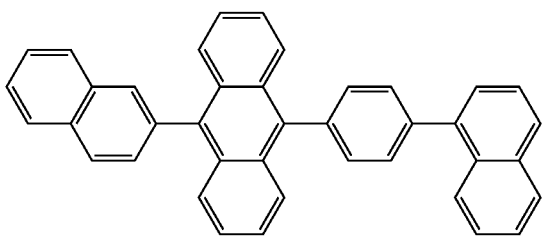

-continued

D-4

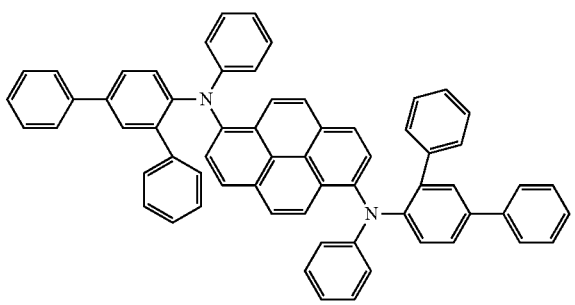

Example 24 and Comparative Examples 13 and 14

In the same manner as in Example 23 except that materials described in Table 5 were used as a second hole transporting layer, light-emitting devices were prepared and evaluated. The results are shown in Table 5.

Examples 25 to 27

Light-emitting devices were prepared in the same manner as in Example 23 except that materials described in Table 5 were used as the second hole transporting layer, and the electron transporting layer was laminated in a two-layer deposited configuration by depositing a compound E-4 or a compound E-2 as a first electron transporting layer in a thickness of 25 nm and depositing a compound E-3 as a second electron transporting layer in a thickness of 10 nm. The results are shown in Table 5.

at a deposition speed ratio of 1:1, and further a dopant was deposited in a doping concentration of 10% by weight. The results are shown in Table 6.

Examples 38 and 39

Light-emitting devices were prepared in the same manner as in Example 1 except that materials described in Table 6 were used as the second hole transporting layer, and the electron transporting layer was laminated in a two-layer deposited configuration by depositing a compound E-2 as a first electron transporting layer in a thickness of 10 nm and depositing a co-deposited film of a compound E-3 and a donor metal (Li: lithium) as a second electron transporting layer in a thickness of 25 nm at a deposition speed ratio of 100:1 (=0.2 nm/s:0.002 nm/s). The results are shown in Table 6.

Examples 40 and 41

Light-emitting devices were prepared in the same manner as in Example 1 except that materials described in Table 6 were used as the second hole transporting layer, a compound [53] and a compound HI-2 were used in place of the compound HI-1 as the hole injection layer, and were deposited in a thickness of 10 nm so that the doping concentration of the compound HI-2 was 2% by weight with respect to the compound [53] in the hole injection layer. The results are shown in Table 6.

Example 42

A light-emitting device were prepared in the same manner as in Example 15 except that as the second hole transporting

TABLE 5

| | Hole injection layer | First hole transporting layer | Second hole transporting layer | Host material | Dopant material | Electron transporting layer | Emitted color | Luminous efficiency (lm/W) | Luminance half-value period (h) |
|---|---|---|---|---|---|---|---|---|---|
| Example 23 | HI-1 | HT-4 | Compound [2] | H-5 | D-4 | E-1/Liq (dope) | Blue | 4.8 | 1800 |
| Example 24 | HI-1 | HT-4 | Compound [31] | H-5 | D-4 | E-1/Liq (dope) | Blue | 5.0 | 2500 |
| Comparative Example 13 | HI-1 | HT-4 | HT-5 | H-5 | D-4 | E-1/Liq (dope) | Blue | 2.9 | 1300 |
| Comparative Example 14 | HI-1 | HT-4 | HT-6 | H-5 | D-4 | E-1/Liq (dope) | Blue | 3.0 | 1200 |
| Example 25 | HI-1 | HT-4 | Compound [2] | H-5 | D-4 | First layer E-4 Second layer E-3 | Blue | 5.0 | 1700 |
| Example 26 | HI-1 | HT-4 | Compound [31] | H-5 | D-4 | First layer E-4 Second layer E-3 | Blue | 5.2 | 2600 |
| Example 27 | HI-1 | HT-4 | Compound [31] | H-5 | D-4 | First layer E-2 Second layer E-3 | Blue | 5.1 | 2600 |

Examples 28 to 35

Light-emitting devices were prepared in the same manner as in Example 1 except that materials described in Table 6 were used as a second hole transporting layer. The results are shown in Table 6.

Examples 36 and 37

Light-emitting devices were prepared in the same manner as in Example 1 except that materials described in Table 6 were used as the second transporting layer, and a mixed host of a compound H-2 and a compound H-3 was used in place of the compound H-1 as a host material. A co-deposited film of the compound H-2 and the compound H-3 was deposited layer, a compound [35] was used in place of the compound [2]. The results are shown in Table 6.

Example 43

A light-emitting device were prepared in the same manner as in Example 16 except that as the second hole transporting layer, a compound [35] was used in place of the compound [2]. The results are shown in Table 6.

Example 44

A light-emitting device were prepared in the same manner as in Example 17 except that as the second hole transporting layer, a compound [35] was used in place of the compound [2]. The results are shown in Table 6.

TABLE 6

| | Hole injection layer | First hole transporting layer | Second hole transporting layer | Host material | Dopant material | Electron transporting layer | Emitted color | Luminous efficiency (lm/W) | Luminance half-value period (h) |
|---|---|---|---|---|---|---|---|---|---|
| Example 28 | HI-1 | HT-4 | Compound [35] | H-1 | D-1 | E-1/Liq (dope) | Green | 44.0 | 3300 |
| Example 29 | HI-1 | HT-4 | Compound [40] | H-1 | D-1 | E-1/Liq (dope) | Green | 40.0 | 2700 |
| Example 30 | HI-1 | HT-4 | Compound [44] | H-1 | D-1 | E-1/Liq (dope) | Green | 44.0 | 3400 |
| Example 31 | HI-1 | HT-4 | Compound [46] | H-1 | D-1 | E-1/Liq (dope) | Green | 50.0 | 4000 |
| Example 32 | HI-1 | HT-4 | Compound [48] | H-1 | D-1 | E-1/Liq (dope) | Green | 43.0 | 3000 |
| Example 33 | HI-1 | HT-4 | Compound [50] | H-1 | D-1 | E-1/Liq (dope) | Green | 44.0 | 3300 |
| Example 34 | HI-1 | HT-4 | Compound [53] | H-1 | D-1 | E-1/Liq (dope) | Green | 51.0 | 4100 |
| Example 35 | HI-1 | HT-4 | Compound [57] | H-1 | D-1 | E-1/Liq (dope) | Green | 51.0 | 4000 |
| Example 36 | HI-1 | HT-4 | Compound [53] | H-2/H-3 | D-1 | E-1/Liq (dope) | Green | 52.0 | 5000 |
| Example 37 | HI-1 | HT-4 | Compound [54] | H-2/H-3 | D-1 | E-1/Liq (dope) | Green | 50.0 | 4900 |
| Example 38 | HI-1 | HT-4 | Compound [53] | H-1 | D-1 | First layer E-4 Second layer E-3/Li (dope) | Green | 52.0 | 4800 |
| Example 39 | HI-1 | HT-4 | Compound [57] | H-1 | D-1 | First layer E-4 Second layer E-3/Li (dope) | Green | 51.0 | 4700 |
| Example 40 | Compound [53]/HI-2 | HT-4 | Compound [47] | H-1 | D-1 | E-1/Liq (dope) | Green | 42.0 | 3100 |
| Example 41 | Compound [53]/HI-2 | HT-4 | Compound [53] | H-1 | D-1 | E-1/Liq (dope) | Green | 53.0 | 5100 |
| Example 42 | HI-1 | HT-4 | Compound [35] | H-2 | D-2 | E-3 | Green | 45.0 | 2800 |
| Example 43 | HI-1 | HT-4 | Compound [35] | H-2/H-3 | D-2 | E-3 | Green | 41.0 | 4000 |
| Example 44 | HI-1 | HT-4 | Compound [35] | H-2 | D-2 | E-1/Liq (dope) | Green | 45.0 | 5000 |

The invention claimed is:

1. A light-emitting device material comprising a compound represented by the following general formula (1):

[Chemical Formula 1]

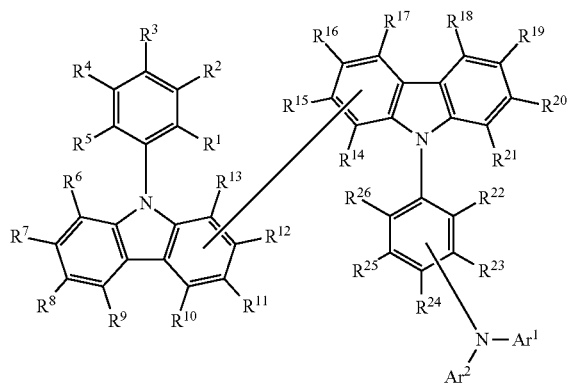

(1)

wherein:
(i) $R^1$ to $R^{21}$ are all hydrogen, and among $R^{22}$ to $R^{26}$, one of $R^{23}$ and $R^{25}$ is $NAr^1Ar^2$ and others are all hydrogen, wherein $Ar^1$ and $Ar^2$ may be the same or different and each represent a substituted or unsubstituted phenyl group; or (ii) $R^1$ to $R^{21}$ may be the same or different and are each selected from the group consisting of hydrogen, an alkyl group, a cycloalkyl group, a heterocyclic group, an alkenyl group, a cycloalkenyl group, an alkynyl group, a halogen, a carbonyl group, a carboxyl group, an oxycarbonyl group, a carbamoyl group, a silyl group and —P(=O)$R^{27}R^{28}$, wherein $R^{27}$ and $R^{28}$ are each an aryl group or a heteroaryl group, with the proviso that two carbazole skeletons are coupled at one of $R^6$ to $R^{13}$ and one of $R^{14}$ to $R^{21}$; and $R^{22}$ to $R^{26}$ satisfy requirement (B):

(B) $R^{24}$ is $NAr^1Ar^2$, others may be the same or different and are each selected from the group consisting of hydrogen, an alkyl group, a cycloalkyl group, a heterocyclic group, an alkenyl group, a cycloalkenyl group, an alkynyl group, a halogen, a carbonyl group, a carboxyl group, an oxycarbonyl group, a carbamoyl group, a silyl group and —P(=O)$R^{27}R^{28}$, and one of $Ar^1$ and $Ar^2$ is an unsubstituted phenyl group, and the other is a phenyl group substituted with an alkyl group, a phenyl group substituted with a halogen, or a phenyl group substituted with a phenyl group.

2. The light-emitting device material according to claim 1, wherein triplet energy of the compound represented by the general formula (1) is 2.60 eV or more.

3. The light-emitting device material according to claim 1, wherein the compound represented by the general formula (1) is a compound represented by the following general formula (2):

[Chemical Formula 2]

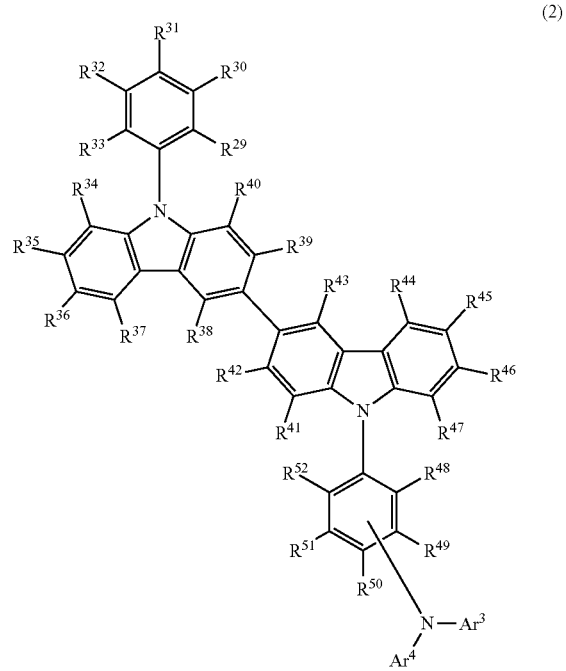

(2)

wherein:
(i) $R^{29}$ to $R^{47}$ are all hydrogen, and among $R^{48}$ to $R^{52}$, one of $R^{49}$ and $R^{51}$ is $NAr^3Ar^4$ and others are all hydrogen, wherein $Ar^3$ and $Ar^4$ may the same or different and each represent a substituted or unsubstituted phenyl group; or (ii) $R^{29}$ to $R^{47}$ may be the same or different and are each selected from the group consisting of hydrogen, an alkyl group, a cycloalkyl group, a heterocyclic group, an alkenyl group, a cycloalkenyl group, an alkynyl group, a halogen, a carbonyl group, a carboxyl group, an oxycarbonyl group, a carbamoyl group, a silyl group and $-P(=O)R^{53}R^{54}$, wherein $R^{53}$ and $R^{54}$ are each an aryl group or a heteroaryl group; and $R^{48}$ to $R^{52}$ satisfy requirement (B'):

(B') $R^{50}$ is $NAr^3Ar^4$, others may be the same or different and are each selected from the group consisting of hydrogen, an alkyl group, a cycloalkyl group, a heterocyclic group, an alkenyl group, a cycloalkenyl group, an alkynyl group, a halogen, a carbonyl group, a carboxyl group, an oxycarbonyl group, a carbamoyl group, a silyl group and $-P(=O)R^{53}R^{54}$, and one of $Ar^3$ and $Ar^4$ is an unsubstituted phenyl group, and the other is a phenyl group substituted with an alkyl group, a phenyl group substituted with a halogen, or a phenyl group substituted with a phenyl group.

4. The light-emitting device material according to claim 1, wherein $R^1$ to $R^{21}$ are all hydrogen, and among $R^{22}$ to $R^{26}$, one of $R^{23}$ and $R^{25}$ is $NAr^1Ar^2$ and others are all hydrogen, and $Ar^1$ and $Ar^2$ are each an unsubstituted phenyl group, a phenyl group substituted with a phenyl group, a phenyl group substituted with an alkyl group, or a phenyl group substituted with a halogen.

5. The light-emitting device material according to claim 1, wherein in the general formula (1), $R^{22}$ to $R^{26}$ satisfy the requirement (B), $R^1$ to $R^{21}$ are all hydrogen, and among $R^{22}$ to $R^{26}$, $R^{24}$ is $NAr^jAr^2$ and others are all hydrogen.

6. The light-emitting device material according to claim 1, wherein $Ar^1$ and $Ar^2$ are different from each other.

7. A light-emitting device which has an organic layer between an anode and a cathode and emits light by means of electric energy, wherein the light-emitting device contains the light-emitting device material according to claim 1 in any of the layers between the anode and the cathode.

8. The light-emitting device according to claim 7, wherein at least a hole transporting layer exists on the organic layer, and the hole transporting layer contains a light-emitting device material comprising a compound represented by the following general formula (1):

[Chemical Formula 1]

(1)

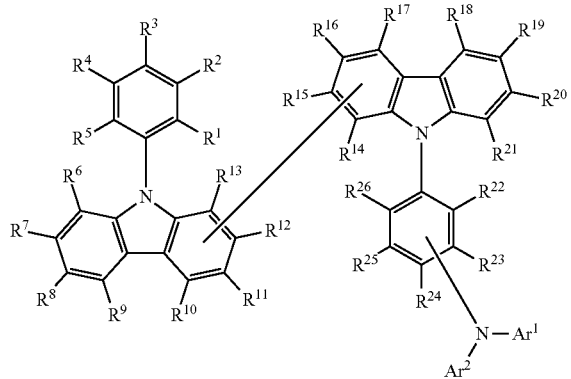

wherein:
(i) $R^1$ to $R^{21}$ are all hydrogen and among $R^{22}$ to $R^{26}$, one of $R^{23}$ and $R^{25}$ is $NAr^jAr^2$ and others are all hydrogen, wherein $Ar^1$ and $Ar^2$ may be the same or different and each represent a substituted or unsubstituted phenyl group; or (ii) $R^1$ to $R^{21}$ may be the same or different and are each selected from the group consisting of hydrogen, an alkyl group, a cycloalkyl group, a heterocyclic group, an alkenyl group, a cycloalkenyl group, an alkynyl group, a halogen, a carbonyl group, a carboxyl group, an oxycarbonyl group, a carbamoyl group, a silyl group and $-P(=O)R^{27}R^{28}$ wherein $R^{27}$ and $R^{28}$ are each an wherein:
(i) $R^1$ to $R^{21}$ are all hydrogen, and among $R^{22}$ to $R^{26}$, one of $R^{23}$ and $R^{25}$ is $NAr^1Ar^2$ and others are all hydrogen, wherein $Ar^1$ and $Ar^2$ may be the same or different and each represent a substituted or unsubstituted phenyl group; or (ii) $R^1$ to $R^{21}$ may be the same or different and are each selected from the group consisting of hydrogen, an alkyl group, a cycloalkyl group, a heterocyclic group, an alkenyl group, a cycloalkenyl group, an alkynyl group, a halogen, a carbonyl group, a carboxyl group, an oxycarbonyl group, a carbamoyl group, a silyl group and $-P(=O)R^{27}R^{28}$, wherein $R^{27}$ and $R^{28}$ are each an aryl group or a heteroaryl group, with the proviso that two carbazole skeletons are coupled at one of $R^6$ to $R^{13}$ and one of $R^{14}$ to $R^{21}$; and $R^{22}$ to $R^{26}$ satisfy requirement (B):

(B) $R^{24}$ is $NAr^1Ar^2$, others may be the same or different and are each selected from the group consisting of hydrogen, an alkyl group, a cycloalkyl group, a heterocyclic group, an alkenyl group, a cycloalkenyl group, an alkynyl group, a halogen, a carbonyl group, a carboxyl group, an oxycarbonyl group, a carbamoyl group, a silyl group and $-P(=O)R^{27}R^{28}$, and one of $Ar^1$ and $Ar^2$ is an unsubstituted phenyl group, and the other is a phenyl group substituted with an alkyl group, a phenyl group substituted with a halogen, or a phenyl group substituted with a phenyl group.

9. The light-emitting device according to claim 7, wherein at least a hole injection layer exists on the organic layer, and the hole injection layer contains a light-emitting device material comprising a compound represented by the following general formula (1):

[Chemical Formula 1]

(1)

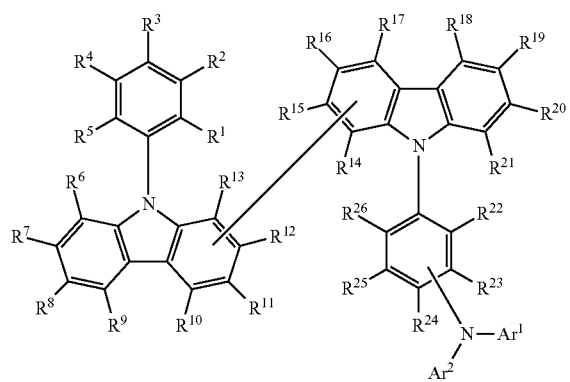

aryl group or a heteroaryl group, with the proviso that two carbazole skeletons are coupled at one of $R^6$ to $R^{13}$ and one of $R^{14}$ to $R^{21}$; and $R^{22}$ to $R^{26}$ satisfy requirement (B):

(B) $R^{24}$ is $NAr^1Ar^2$, others may be the same or different and are each selected from the group consisting of hydrogen, an alkyl group, a cycloalkyl group, a heterocyclic group, an alkenyl group, a cycloalkenyl group, an alkynyl group, a halogen, a carbonyl group, a carboxyl group, an oxycarbonyl group, a carbamoyl group, a silyl group and $-P(=O)R^{27}R^{28}$, and one of $Ar^1$ and $Ar^2$ is an unsubstituted phenyl group, and the other is a phenyl group substituted with an alkyl group, a phenyl group substituted with a halogen, or a phenyl group substituted with a phenyl group.

10. The light-emitting device according to claim 9, wherein a hole injection layer exists between the hole transporting layer and the anode, and the hole injection layer contains an acceptor material.

11. The light-emitting device according to claim 8, wherein at least an emissive layer exists on the organic layer, and the emissive layer contains a triplet emissive material.

12. The light-emitting device according to claim 11, wherein the triplet emissive material is a metal complex containing iridium or platinum.

13. The light-emitting device according to claim 7, wherein at least an electron transporting layer exists on the organic layer, and the electron transporting layer contains a compound containing electron-accepting nitrogen and having a heteroaryl ring structure composed of devices selected from carbon, hydrogen, nitrogen, oxygen, silicon and phosphorus.

14. The light-emitting device according to claim 13, wherein the electron transporting layer contains a donor material.

* * * * *